(12) United States Patent
Gildersleeve et al.

(10) Patent No.: US 9,804,163 B2
(45) Date of Patent: Oct. 31, 2017

(54) BIOMARKERS FOR PROSTATE CANCER AND METHODS FOR THEIR DETECTION

(75) Inventors: Jeffrey Gildersleeve, Frederick, MD (US); Christopher Campbell, Baltimore, MD (US); Oyindasola Oyelaran, Boston, MA (US); James Gulley, Takoma Park, MD (US); Jeffrey Schlom, Potomac, MD (US)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 438 days.

(21) Appl. No.: 13/814,337

(22) PCT Filed: Aug. 5, 2011

(86) PCT No.: PCT/US2011/046799
§ 371 (c)(1),
(2), (4) Date: Mar. 5, 2013

(87) PCT Pub. No.: WO2012/019125
PCT Pub. Date: Feb. 9, 2012

(65) Prior Publication Data
US 2013/0156813 A1 Jun. 20, 2013

Related U.S. Application Data

(60) Provisional application No. 61/371,537, filed on Aug. 6, 2010, provisional application No. 61/443,955, filed on Feb. 17, 2011.

(51) Int. Cl.
| | |
|---|---|
| *A61K 39/00* | (2006.01) |
| *C07K 14/705* | (2006.01) |
| *C07K 16/00* | (2006.01) |
| *C07K 16/30* | (2006.01) |
| *G01N 33/574* | (2006.01) |

(52) U.S. Cl.
CPC .... *G01N 33/57434* (2013.01); *A61K 39/0011* (2013.01); *G01N 33/57469* (2013.01); *A61K 2039/5252* (2013.01); *A61K 2039/5256* (2013.01); *A61K 2039/545* (2013.01); *A61K 2039/55583* (2013.01); *A61K 2039/575* (2013.01); *A61K 2039/585* (2013.01); *C12N 2710/24043* (2013.01); *C12N 2710/24143* (2013.01); *G01N 2400/02* (2013.01); *G01N 2800/52* (2013.01)

(58) Field of Classification Search
None
See application file for complete search history.

(56) References Cited

U.S. PATENT DOCUMENTS

| | | |
|---|---|---|
| 6,001,349 A | 12/1999 | Panicali et al. |
| 6,045,802 A | 4/2000 | Schlom et al. |
| 6,165,460 A | 12/2000 | Schlom et al. |
| 6,258,540 B1 * | 7/2001 | Lo ........................ C12Q 1/6879 435/440 |
| 6,548,068 B1 | 4/2003 | Schlom et al. |
| 6,756,038 B1 | 6/2004 | Schlom et al. |
| 6,893,869 B2 | 5/2005 | Schlom et al. |
| 6,946,133 B1 | 9/2005 | Schlom et al. |
| 6,969,609 B1 | 11/2005 | Schlom et al. |
| 7,118,738 B2 | 10/2006 | Schlom et al. |
| 7,892,752 B2 | 2/2011 | Dwek et al. |
| 2003/0003079 A1 | 1/2003 | Schlom et al. |
| 2004/0151733 A1 | 8/2004 | Livingston et al. |
| 2005/0163792 A1 | 7/2005 | Young et al. |
| 2005/0186180 A1 | 8/2005 | Schlom et al. |
| 2006/0269974 A1 | 11/2006 | Dwek et al. |
| 2007/0048860 A1 | 3/2007 | Schlom et al. |
| 2007/0098691 A1 | 5/2007 | Schlom et al. |
| 2009/0324619 A1 * | 12/2009 | Hwang .................. A61K 39/00 424/178.1 |

FOREIGN PATENT DOCUMENTS

| | | |
|---|---|---|
| WO | WO 98/04727 A1 | 2/1998 |
| WO | WO 2006/114659 A1 | 11/2006 |
| WO | WO 2009/035494 A2 | 3/2009 |

OTHER PUBLICATIONS

Smorodin et al. ("Smorodin", Exp. Oncol., 2007, 29, 61-66).*
Slovin et al. ("Slovin", Immun. and Cell Bio., 2005, 83, 418-428).*
Madan et al ("Madan", Expert. Opin. Investig. Drugs, 2009, 18, 1001-1011).*
Gulley et al., Cancer Immunol Immunother. May 2010;59(5):663-74. Epub Nov. 5, 2009.*
Arlen et al, ("Alren" J Urol. Oct. 2007;178(4 Pt 1):1515-20. Epub Aug. 16, 2007).*
Dotan et al. ("Dotan", Lupus, 2006, 15, 442-450).*
Pritzker (Clinical Chemistry, 2002, 48:1147-1150).*
Schaffert et al ("Schaffert", Int. J. of Pancreatology 1997, 21, 21-29).*
Oyelarin et al ("Oyelarin", J. Proteome Res, 2009, 8, 3529-3538).*
Campbell et al., "Serum Antibodies to Blood Group A Predict Survival on Prostvac-VF," *Clin. Cancer Res.*, 19(5): 1290-1299 (2013).
Zhang et al. "Supporting Information for Multidimensional Glycan Arrays for Enhanced Antibody Profiling," retrieved from http://www.rsc.org/suppdata/mb/c0/c002259d/c002259d_esi.pdf on Nov. 20, 2012.

(Continued)

*Primary Examiner* — Mark Halvorson
*Assistant Examiner* — Kauser Akhoon
(74) *Attorney, Agent, or Firm* — Leydig, Voit & Mayer, Ltd.

(57) ABSTRACT

The invention provides a method for predicting the clinical response to a cancer vaccine in a patient having cancer, a method for determining the immune response to a cancer vaccine in a patient having cancer who has been administered a cancer vaccine, a method for determining the long-term survival in a patient having cancer, corresponding kits therefor, as well as methods of for improving the efficacy of a virus-based vaccine.

26 Claims, 9 Drawing Sheets

(56) References Cited

OTHER PUBLICATIONS

Figure 1D:
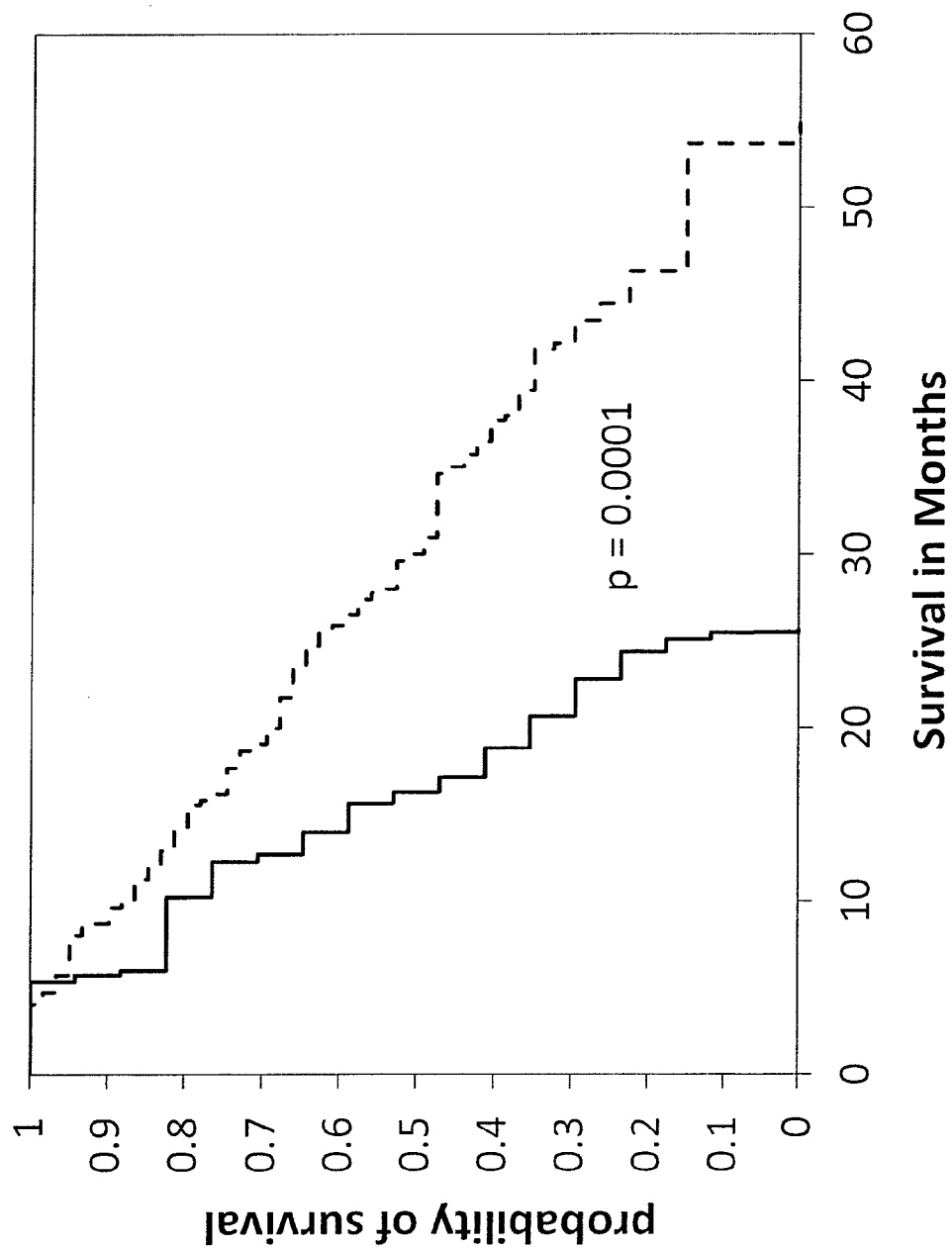

European Patent Office, International Preliminary Report on Patentability in International Application No. PCT/US2011/046799, 9 pages (dated Feb. 21, 2013).
Ariga et al., "Glycosphingolipid antigens in neural tumor cell lines and anti-glycosphingolipid antibodies in sera of patients with neural tumors," *Neurosignals*, 16 (2-3), 226-234 (2008), published online Feb. 5, 2008.
Huflejt et al., "Printed glycan Array Identifies Specific Signatures of anti-glycan autoantibodies as biomarkers in sera of breast cancer patients: Diagnostic, Prognostic and Therapeutic Opportunities," *Cancer Biomarkers Section A of Disease markers*, 2 (5), 187 (2006) poster abstract.
Pierce, "Chapter 16—Cancer Glycomics" in *Handbook of Glycomics*, 399-429 (2010).
Ravindranath et al., "An epitope common to gangliosides O-acetyl-GD3 and GD3 recognized by antibodies in melanoma patients after active specific immunotherapy," *Cancer Res.*, 49 (14), 3891-3897 (1989).
Arlen et al., "A randomized phase II study of concurrent docetaxel plus vaccine versus vaccine alone in metastatic androgen-independent prostate cancer," *Clin. Cancer Res.*, 12(4): 1260-1269 (2006).
Butterfield et al., "Determinant spreading associated with clinical response in dendritic cell-based immunotherapy for malignant melanoma," *Clin. Cancer Res.*, 9(9): 998-1008 (2003).
Copier et al., "Improving the efficacy of cancer immunotherapy," *European Journal of Cancer*, 45: 1424-1431 (2009).
Disis et al., "Generation of T-Cell Immunity to the HER-2/neu Protein After Active Immunization With HER-2/neu Peptide—Based Vaccines," *J. Clin. Oncol.*, 20(11): 2624-2632 (2002).
Dotan et al., "Anti-glycan antibodies as biomarkers for diagnosis and prognosis," *Lupus*, 15(7): 1-10 (2006).
European Patent Office, International Search Report in International Application No. PCT/US2011/046799 (dated Jun. 22, 2012).
Geβner et al., "Enhanced activity of CMP-neuAc:Galβ1-4GlcNAc:α2,6-sialyltransferase in metastasizing human colorectal tumor tissue and serum of tumor patients," *Cancer Letters*, 75: 143-149 (1993).
Keding et al., "Prospects for total synthesis: A vision for a totally synthetic vaccine targeting epithelial tumors," *Proc. Natl. Acad. Sci. USA*, 101(33): 11937-11942 (2004).
Li et al., "GalNAcα1-3Gal, a new prognostic marker for cervical cancer," *International Journal of Cancer*, 126(2): 459-468 (2010).
Livingston et al., "Carbohydrate vaccines that induce antibodies against cancer. 1. Rationale," *Cancer Immunol. Immunother.*, 45: 1-9 (1997).
Oyelaran et al., "Microarrays with varying carbohydrate density reveal distinct subpopulations of serum antibodies," *J. Proteome Res.*, 8: 3529-3538 (2009).
Ranieri et al., "Dendritic cell/peptide cancer vaccines: Clinical responsiveness and epitope spreading," *Immunol. Invest.*, 29(2): 121-125 (2000).
Schwarz et al., "A new kind of carbohydrate array, its use for profiling antiglycan antibodies, and the discovery of a novel human cellulose-binding antibody," *Glycobiology*, 13(11): 749-754 (2003).
Stäger et al., "Natural antibodies and complement are endogenous adjuvants for vaccine-induced CD8+ T-cell responses," *Nat. Med.*, 9(10): 1287-1292 (2003).
Wang et al., "Glycan microarray of Globo H and related structures for quantitative analysis of breast cancer," *Proc. Natl. Acad. Sci. USA*, 105(33): 11661-11666 (2008).
Wierecky et al., "Dendritic cell-based cancer immunotherapy targeting MUC-1," *Cancer Immunol. Immunother.*, 55(1): 63-67 (2006).
Zhang et al., "Antibodies against GD2 ganglioside can eradicate syngeneic cancer micrometastases," *Cancer Research*, 58(13): 2844-2849 (1998).
Zhang et al., "Multidimensional glycan arrays for enhanced antibody profiling," *Molecular BioSystems*, 6(9): 1583-1591 (2010).
Campbell et al., "Humoral response to a viral glycan correlates with survival on PROSTVAC-VF," *PNAS*, 111 (17), E1749-E1758 (2014) with Correction.
Slovin et al., "A polyvalent vaccine for high-risk prostate patients: 'are more antigens better?'," *Cancer Immunol. Immunother.*, 56: 1921-1930 (2007).
European Patent Office, Partial European Search Report in Application No. 16199473.6 (dated Feb. 6, 2017).
Pending U.S. Appl. No. 15/345,634, filed Nov. 8, 2016.

\* cited by examiner

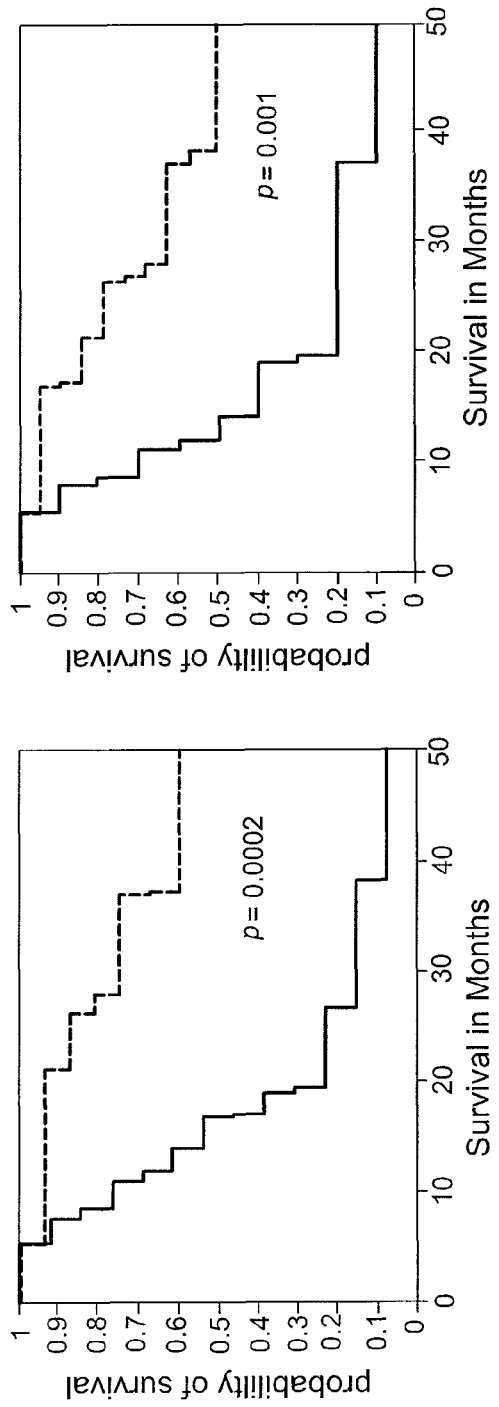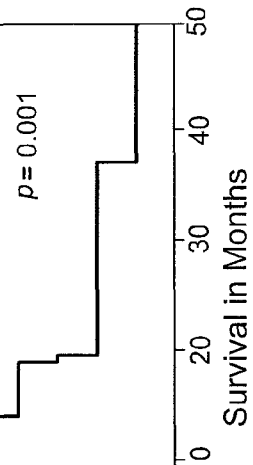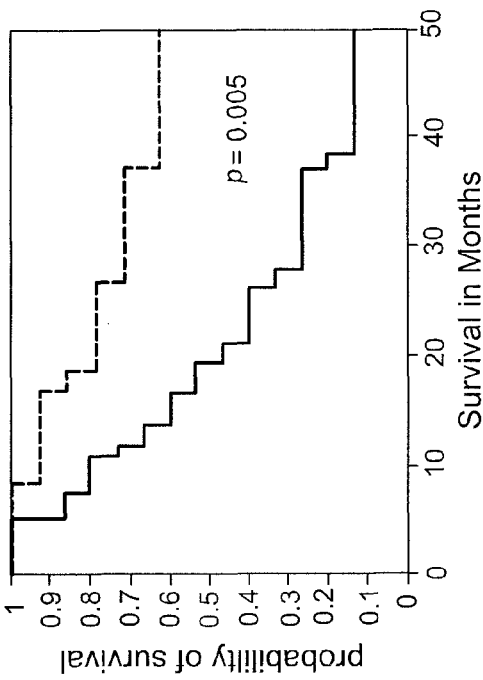

Fig. 2

| Group | Abbreviations | Description |
|---|---|---|
| Carbohydrates | 3'SLacNAc | Sialylα2-3Galβ1-4GlcNAc |
| | 3'Sia-3-FL | Siaα2-3Galβ1-4(Fucα1-3)Glc |
| | 3'-sulpho-LeA | 3-SO3-Galβ1-3[Fucα1-4)GlcNAc- |
| | 3'-sulpho-LeX | 3-SO3-Galβ1-4[Fucα1-3)GlcNAc- |
| | 6'Slac | Sialylα2-6Galβ1-4Glc |
| | 6'-sulpho-LeA | 6-SO3-Galβ1-3[Fucα1-4)GlcNAc- |
| | 6'-sulpho-LeX | 6-SO3-Galβ1-4[Fucα1-3)GlcNAc- |
| | 2FucLac | Fucα1-2Galβ1-4Glc- |
| | Adi | GalNAcα1-3Galβ-BSA |
| | A-LeB hexa | GalNAcα1-3(Fucα1-2)Galβ1-3(Fucα1-4)GlcNAcβ1-3Galβ1- |
| | alphaGal | Galα1-3Galβ1-4GlcNAc- |
| | alphaGal-6-deoxy | Galα1-3Galβ1-4(6deoxy-GlcNAc)- |
| | Ara5 | Araα1-5Araα1-5Araα1-5Araα1-5Araα1- |
| | Bdi | Galα1-3Gal- |
| | BG-A | GalNAcα1-3(Fucα1-2)Galβ- |
| | BG-A1 | GalNAcα1-3(Fucα1-2)Galβ1-3GlcNAcβ1-3Galβ1-4(Glc)- |
| | BG-B (Dextra) | Galα1-3(Fucα1-2)Galβ-BSA from Dextra |
| | BG-B (EMD) | Galα1-3(Fucα1-2)Galβ-BSA from EMD |
| | BG-H1 | Fucα1-2Galβ1-3GlcNAcβ1-3Galβ1-4Glcβ- |
| | BG-H2 | Fucα1-2Galβ1-4GlcNAcβ- |
| | Cellobiose | Glcβ1-4Glcβ- |
| | Cellotriose | Glcβ1-4Glcβ1-4Glcβ- |
| | Chito 3 | GlcNAcβ1-4GlcNAcβ1-4GlcNAcβ-BSA (8/BSA) |
| | Chito 3 - 20 | GlcNAcβ1-4GlcNAcβ1-4GlcNAcβ-BSA (20/BSA) |
| | DSLNT | Siaα2-3Galβ1-3(Siaα2-6)GlcNAcβ1-3Galβ1- |
| | Forssman Di | GalNAcα1-3GalNAcβ1- |
| | Fuc-a | Fuc-α - |
| | Fuc-b | Fuc-β - |
| | Fuc_Sia-LNnH | Galβ1-4[Fucα1-3]GlcNAcβ1-6[Neu5Acα2-3Galβ1-4GlcNAcβ1-3]Galβ1- |
| | G2M4 | Manβ1-4(Galα1-6)Manβ1-4(Galα1-6)Manβ1-4Manβ1- |

Fig. 2 (continued)

| Group | Abbreviations | Description |
|---|---|---|
| | GA1 | Galβ1-3GalNAcβ1-4Galβ1- |
| | GA1di | Galβ1-3GalNAcβ – |
| | GA2di | GalNAcβ1-4Galβ |
| | Gal3 | Galα1-3Galβ1-4Galα- |
| | Gal-a | Gal-α - |
| | Galα1-2Gal | Galα1-2Gal- |
| | Galα1-4Galb | Galα1-4Galβ- |
| | Galα3-type1 | Galα1-3Galβ1-3GlcNAc- |
| | Gal-b | Gal-β - |
| | Galb1-6Man-a | Galβ1-6Man-α - |
| | Galili | Galα1-3Galβ1-4Glc- |
| | GalNAc-a | GalNAc-α - |
| | GalNAcα1-6Galb | GalNAcα1-6Galβ |
| | GalNAc-b | GalNAc-β - |
| | Gb4 | GalNAcβ1-3Galα1-4Galβ1- |
| | Glc-a | Glc-α - |
| | Glcα1-6Glcα1-4Glcα1-4Glcb | Glcα1-6Glcα1-4Glcα1-4Glcβ- |
| | Glc-b | Glc-β - |
| | GlcNAcα1-4Galb | GlcNAcα1-4Galβ- |
| | GlcNAc-b | GlcNAc-β - |
| | GlcNAc-Man3 | Manα1-6(GlcNAcβ1-2Manα1-3)Manβ1-4GlcNAcβ- |
| | GlcNAc-Man5 | Manα1-6(Manα1-3)Manα1-6(GlcNAcβ1-2Manα1-3)Manβ1-4GlcNAcβ- |
| | GM1 | Galβ1-3GalNAcβ1-4(Siaα2-3)Galβ-4(Glc)- |
| | GM3 | Sialylα2-3Galβ1-4Glc- |
| | Hep-N-acetylated | fully N-acetylated heparin polysaccharide |
| | Hep-5000 | heparin polysaccharide (MW ~5000) |
| | Hya8 | (GlcNAcβ1-4GlcAβ1-3)₄β1- |
| | Hya9 | (GlcAβ1-3GlcNAcβ1-4)₄β1-3GlcAβ1- |
| | Hybrid-M5N4B | GlcNAcβ1-2Manα1-3[Manα1-3(Manα1-6)Manα1-6](GlcNAcβ1-4)Manβ1-4GlcNAcβ1- |

Fig. 2 (continued)

| Group | Abbreviations | Description |
|---|---|---|
| | iLNO | Galβ1-3GlcNAcβ1-3Galβ1-4GlcNAcβ1-6 (Galβ1-3GlcNAcβ1-3)Galβ1- |
| | Isomaltose | Glcα1-6Glcβ- |
| | LacNAc | Galβ1-4GlcNAc – |
| | LacNAc (trimeric) | Galβ1-4GlcNAcβ1-3Galβ1-4GlcNAcβ1-3Galβ1-4GlcNAcβ- |
| | LacNAc-Man5 | Manα1-6(Manα1-3)Manα1-6(Galβ1-4GlcNAcβ1-2Manα1-3)Manβ1-4GlcNAcβ- |
| | Lactose | Galβ1-4Glcβ- – |
| | LeA | Galβ1-3[Fucα1-4]GlcNAcβ1-3Galβ1-4Glcβ- |
| | LeA-LeX | Galb1-3(Fucα1-4)GlcNAcb1-3Galb1-4(Fucα1-3)GlcNAcb1-3Galb1- |
| | LeB | Fucα1-2Galβ1-3[Fucα1-4)GlcNAcβ1-3Galβ1-4Glcβ- |
| | LeC | Galβ1-3GlcNAcβ- |
| | LeX (dimeric) | Galβ1-4[Fucα1-3)GlcNAcβ1-3Galβ1-4(Fucα1-3)GlcNAcβ1-3Galβ1- |
| | LeX (monomeric) | Galβ1-4[Fucα1-3)GlcNAc-APD- |
| | LeY | Fucα1-2Galβ1-4[Fucα1-3)GlcNAc – |
| | LNH | Galβ1-4GlcNAcβ1-6(Galβ1-3GlcNAcβ1-3)Galβ1- |
| | LNnH | Galβ1-4GlcNAcβ1-6(Galβ1-4GlcNAcβ1-3)Galβ1- |
| | LNnT | Galβ1-4GlcNAcβ1-3Galβ1- |
| | LNT | Galβ1-3GlcNAcβ1-3Galβ- |
| | LSTa | Siaα2-3Galβ1-3GlcNAcβ1-3Galβ1- |
| | LSTb | Galβ1-3(Siaα2-6)GlcNAcβ1-3Galβ1- |
| | LSTc | Siaα2-6Galβ1-3GlcNAcβ1-3Galβ1- |
| | Maltopentaose | Glcα1-4Glcα1-4Glcα1-4Glcα1-4Glcα- |
| | Maltose | Glcα1-4Glcβ- |
| | Man3 | Manα1-6(Manα1-3)Manβ1-4GlcNAc - |
| | Man5 | Manα1-6(Manα1-3)Manα1-6(Manα1-3)Manβ1-4GlcNAc- |
| | Man6 - II | Manα1-3Manα1-3Manα1-6(Manα1-6(Manα1-3)Manβ1- |
| | Man6 - I | Manα1-6(Manα1-3)Manα1-6(Manα1-2Manα1-3)Manβ1- |
| | Man7D1 | Manα1-6(Manα1-3)Manα1-6(Manα1-2Manα1-2Manα1-3)Manβ1-4GlcNAc- |
| | Man7D3 | Manα1-2Manα1-6(Manα1-3)Manα1-6(Manα1-2Manα1-3)Manβ1-4GlcNAc- |
| | Man8D1D3 | Manα1-2Manα1-6(Manα1-3)Manα1-6(Manα1-2Manα1-2Manα1-3)Manβ1-4GlcNAc- |

Fig. 2 (continued)

| Group | Abbreviations | Description |
|---|---|---|
| | Man9 | Manα1-2Manα1-6(Manα1-2Manα1-3)Manα1-6(Manα1-2Manα1-2Manα1-3)Manβ1-4GlcNAc- |
| | Man-a | Man-α - |
| | Manα1-6Man-a | Manα1-6Man-α - |
| | Manb4 | Manβ1-4Manβ1-4Manβ1-4Manβ1- |
| | ManT | Manα1-6[Manα1-3]Manβ - |
| | MFLNH I | Galβ1-4GlcNAcβ1-6 (Fucα1-2Galβ1-3GlcNAcβ1-3)Galβ1- |
| | MFLNH III | Galβ1-4(Fucα1-2)GlcNAcβ1-6 (Galβ1-3GlcNAcβ1-3)Galβ1- |
| | MSMFLNH I | Siaα2-6Galβ1-4GlcNAcβ1-6 (Fucα1-2Galβ1-3GlcNAcβ1-3)Galβ1- |
| | MSMFLnNH | Galβ1-4(Fucα1-3)GlcNAcβ1-6 (Siaα1-3Galβ1-4GlcNAcβ1-3)Galβ1- |
| | NA2 | Galβ1-4GlcNAcβ1-2Manα1-6[Galβ1-4GlcNAcβ1-2Manα1-3]Manβ1-4GlcNAc - |
| | NA3 | Galβ1-4GlcNAcβ1-2Manα1-6[Galβ1-4GlcNAcβ1-2(Galβ1-4GlcNAcβ1-2)Manα1-3]Manβ1-4GlcNAc |
| | NA4 | Galβ1-4GlcNAcβ1-2(Galβ1-4GlcNAcβ1-6)Manα1-6[Galβ1-4GlcNAcβ1-2(Galβ1-4GlcNAcβ1-4)Manα1-3]Manβ1-4GlcNAc - |
| | NGA2 | GlcNAcβ1-2Manα1-6(GlcNAcβ1-2Manα1-3)Manβ1-4GlcNAc - |
| | NGA2B | GlcNAcβ1-2Manα1-6(GlcNAcβ1-2Manα1-3)(GlcNAcβ1-4)Manβ1-4GlcNAc - |
| | NGA3 | GlcNAcβ1-2Manα1-6(GlcNAcβ1-2(GlcNAcβ1-4)Manα1-3)Manβ1-4GlcNAc - |
| | NGA3B | GlcNAcβ1-2Manα1-6(GlcNAcβ1-2(GlcNAcβ1-4)Manα1-3)(GlcNAcβ1-4)Manβ1-4GlcNAc- |
| | NGA4 | GlcNAcβ1-2(GlcNAcβ1-6)Manα1-6[GlcNAcβ1-2(GlcNAcβ1-4)Manα1-3]Manβ1-4GlcNAc- |
| | NGA4(B)2 | GlcNAcβ1-2(GlcNAcβ1-4)(GlcNAcβ1-6)Manα1-6[GlcNAcβ1-2Manα1-3](GlcNAcβ1-4)Manβ1-4GlcNAc - |
| | NGA5B | GlcNAcβ1-2(GlcNAcβ1-4)(GlcNAcβ1-6)Manα1-6[GlcNAcβ1-2(GlcNAcβ1-4)Manα1-3](GlcNAcβ1-4)Manβ1-4GlcNAc |
| | P1 | Galα1-4Galβ1-4GlcNAc- |
| | Pk or Gb3 | Galα1-4Galβ1-4Glc- |
| | pLNH | Galβ1-3GlcNAcβ1-3Galβ1-4GlcNAcβ1-3Galβ1- |
| | Rha-a | Rha-α - |
| | Rha-b | Rha-β - |

Fig. 2 (continued)

| Group | Abbreviations | Description |
|---|---|---|
| | Sialyl LeA | Siaα2-3Galβ1-3[Fucα1-4]GlcNAcβ1-3Galβ1- |
| | Sialyl LeX | Sialylα2-3Galβ1-4[Fucα1-3]GlcNAc – |
| | TFiLNO(1-2,1-2,1-3) | Fucα1-2Galβ1-3GlcNAcb1-3Galb1-4(Fucα1-3)GlcNAcb1-6(Fucα1-2Galb1-3GlcNAcb1-3)Galb- |
| | Sia-LNnT | Siaα2-3Galβ1-4GlcNAcβ1-3Galβ1- |
| | Sia-LNF V | Fucα1-2Galβ1-3[Neu5Acα2-6]GlcNAcβ1-3Galβ1- |
| | X3Glc3 | Xylα1-6Glcβ1-4(Xylα1-6)Glcβ1-4(Xylα1-6)Glcβ1- |
| | Xylβ4 | Xylβ1-4Xylβ1-4Xylβ1-4Xylβ1- |
| Glycoproteins | AGE30 | Advanced glycation endproducts- Glucose + BSA on day 30 (AGE30) |
| | AGE60 | Advanced glycation endproducts- Glucose + BSA on day 60 (AGE60) |
| | AGE90 | Advanced glycation endproducts- Glucose + BSA on day 90 (AGE90) |
| | Alpha-1-acid glycoprotein | alpha1 Acid Glycoprotein |
| | Alpha-fetoprotein | alpha fetoprotein |
| | BSM | Bovine submaxillary mucin |
| | BSM (asialo) | Asialo-Bovine submaxillary mucin |
| | BSM (deacetylated) | Deacetylated-Bovine submaxillary mucin |
| | BSM (ox) | periodate oxidized bovine submaxillary mucin |
| | CEA | carcinoembryonic antigen |
| | FABP | Fatty Acid Binding Protein |
| | fetuin | fetuin |
| | fetuin (asialo) | asialofetuin |
| | Fetuin (ox) | periodate oxidized fetuin |
| | glycophorin (asialo) | asialo-glycophorin A |
| | Glycophorin A | Glycophorin A |
| | hsp90 | Heat Shock Protein 90 |
| | KLH | Keyhole limpet hemocyanin |
| | KLH (oxidized) | periodate oxidized Keyhole limpet hemocyanin |
| | OSM | Ovine submaxillary mucin |
| | OSM (asialo) | asialo-Ovine submaxillary mucin |

Fig. 2 (continued)

| Group | Abbreviations | Description |
|---|---|---|
| | OSM (asialo, enzym) | enzyme treated asialo-OSM |
| | OSM (enzym) | enzyme treated Ovine submaxillary mucin |
| | OSM (ox) | periodate oxidized ovine submaxillary mucin |
| | ovalbumin | ovalbumin |
| | Ovalbumin (ox) | periodate oxidized ovalbumin |
| | PSA | Prostate Specific Antigen; human seminal fluid |
| | Tgl | Thyroglobulin |
| Peptides | Ac-A-Tn(Thr)-S-G | Ac-Ala-(GalNAcα)Thr-Ser-Gly-Hex (SEQ ID NO: 1) |
| | Ac-G-V-Tn(Thr)-S-A-G | Ac-Gly-Val-(GalNAcα)Thr-Ser-Ala-Gly-Hex (SEQ ID NO: 2) |
| | Ac-P-Tn(Thr)-T-G | Ac-Pro-(GalNAcα)Thr-Thr-Gly-Hex (SEQ ID NO: 3) |
| | Ac-S-S-S-G | Ac-Ser-Ser-Ser-Gly-BSA (SEQ ID NO: 4) |
| | Ac-S-TF(Ser)-S-G | AcSer-(Galβ1-3GalNAcα)Ser-Ser-Gly-Hex-BSA (SEQ ID NO: 5) |
| | Ac-S-Thr-S-A-G | Ac-Ser-Thr-Ser-Gly-Hex (SEQ ID NO: 6) |
| | Ac-S-Tn(Ser)-S-G | AcSer-(GalNAcα)Ser-Ser-Gly-Hex-BSA (SEQ ID NO: 7) |
| | Ac-S-Tn(Thr)-A-G | Ac-Ser-(GalNAcα)Thr-Ser-Ala-Gly-Hex (SEQ ID NO: 8) |
| | Ac-S-Tn(Thr)-G-G | Ac-Ser-(GalNAcα)Thr-Gly-Gly-Hex (SEQ ID NO: 9) |
| | Ac-S-Tn(Thr)-S-G | AcSer-(GalNAcα)Thr-Ser-Gly-Hex-BSA (SEQ ID NO: 10) |
| | Ac-S-Tn(Thr)-Tn(Thr)-G | Ac-Ser-(GalNAcα)Thr-(GalNAcα)Thr-Gly-Hex (SEQ ID NO: 11) |
| | Ac-S-Tn(Thr)-V-G | Ac-Ser-(GalNAcα)Thr-Val-Gly-Hex (SEQ ID NO: 12) |
| | Ac-TF(Ser)-G | Ac(Galβ1-3GalNAcα)Ser-Gly-Hex-BSA |
| | Ac-Tn(Ser)Tn(Ser)Tn(Ser)-G | Ac(GalNAcα)Ser-(GalNAcα)Ser-(GalNAcα)Ser-Gly-Hex- (SEQ ID NO: 13) |
| | Ac-Tn(Thr)-G | Ac(GalNAcα)Thr-Gly-Hex- |
| | Ac-T-Tn(Thr)-P-G | Ac-Thr-(GalNAcα)Thr-Pro-Gly-Hex (SEQ ID NO: 14) |
| | Ac-Tn(Thr)-Tn(Thr)-Tn(Thr)-G | Ac-(GalNAcα)Thr-(GalNAcα)Thr-(GalNAcα)Thr-Gly-Hex (SEQ ID NO: 15) |
| | Ac-V-Tn(Thr)-S-G | Ac-Val-(GalNAcα)Thr-Ser-Gly-Hex (SEQ ID NO: 16) |
| | DTVPLPTAHG-TF(Thr)-SASSTG | D-T-V-P-L-P-T-A-H-G-TF(Thr)-S-A-S-S-T-G (SEQ ID NO: 17) |
| | DTVPLPTAHG-TF(Thr)-TF(Ser)-ASSTG | D-T-V-P-L-P-T-A-H-G-TF(Thr)-TF(Ser)-A-S-S-T-G (SEQ ID NO: 18) |

Fig. 2 (continued)

| Group | Abbreviations | Description |
|---|---|---|
| | DTVPLPTAHGTSASSTG | D-T-V-P-L-P-T-A-H-G-T-S-A-S-S-T-G (SEQ ID NO: 19) |
| | DTVPLPTAHGT-TF(Ser)-ASSTG | D-T-V-P-L-P-T-A-H-G-T-TF(Ser)-A-S-S-T-G (SEQ ID NO: 20) |
| | DTVPLP-TF(Thr)-AHGTSASSTG | D-T-V-P-L-P-TF(Thr)-A-H-G-T-S-A-S-S-T-G (SEQ ID NO: 21) |
| Controls | BSA | Bovine serum albumin |
| | BSA-#2 | Bovine serum albumin |
| | Cy3 | Cy3-BSA (20µg/mL + BSA, 125µg/mL total) |
| | Cy5 | Cy5-BSA (30µg/mL + BSA, 125µg/mL total) |
| | HSA | Human serum albumin (isolated from serum) |
| | HSA (recomb) | human serum albumin (recombinant) |
| | PEG-linker | HO-(CH2)2-NH-Gly-CO-PEG7-NH-(CO)Hept-SH-Mal-Cychex-CO-BSA |

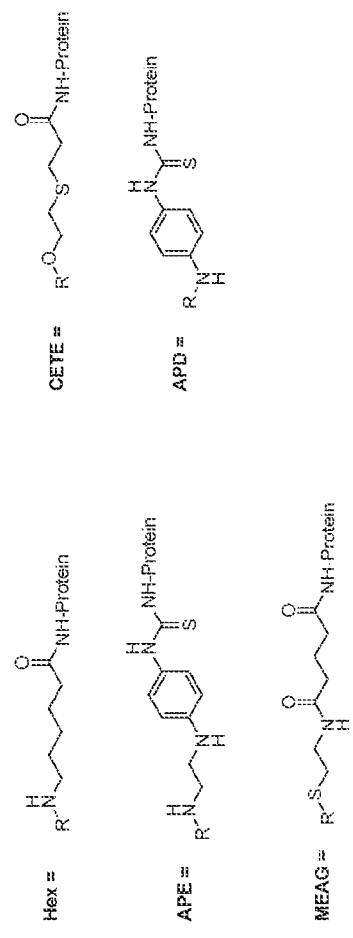

Linkers

BIOMARKERS FOR PROSTATE CANCER AND METHODS FOR THEIR DETECTION

CROSS-REFERENCE TO RELATED APPLICATIONS

This patent application is a U.S. National Phase of International Patent Application No. PCT/US2011/046799, filed Aug. 5, 2011, which claims the benefit of U.S. Provisional Patent Application No. 61/371,537, filed Aug. 6, 2010, and U.S. Provisional Patent Application No. 61/443,955, filed Feb. 17, 2011, which are incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follow: One 7,393 Byte ASCII (Text) file named "712026_ST25.txt," created on Jan. 15, 2013.

Applicants respectfully request entry into the specification of the sequence listing submitted herewith.

BACKGROUND OF THE INVENTION

A cancer vaccine that shows tremendous promise for the treatment of prostate cancer is the PROSTVAC-VF vector-based vaccine. The vaccine is composed of an initial vaccination with a recombinant vaccinia virus containing the human genes for prostate specific antigen (PSA) and three costimulatory molecules (B7.1, LFA-3, and ICAM-1), followed by booster injections with a fowlpox virus with the same four transgenes (see, e.g., Garnett et al., *Curr. Pharm. Des.*, 12: 351-361 (2006), and Madan et al., *Expert Opin. Biol. Ther.*, 10: 19-28 (2010)). The vaccine is designed to stimulate an immune response to prostate tumor cells that express high levels of PSA. The vaccine has been evaluated in several phase I and phase II clinical trials with excellent results (see, e.g., Lechleider et al., *Clin. Cancer Res.*, 14: 5284-5291 (2008), Madan et al., *Clin. Cancer Res.*, 14: 4526-4531 (2008), Garnett et al., *Clin. Cancer Res.*, 14: 3536-3544 (2008), Arlen et al., *J. Urol.*, 178: 1515-1520 (2007), Theoret et al., *Clin. Genitourin. Cancer*, 5: 347-350 (2007), and Arlen et al., *Clin. Cancer Res.*, 12: 1260-1269 (2006)).

BRIEF SUMMARY OF THE INVENTION

The invention provides a method for predicting the clinical response to a cancer vaccine in a patient having cancer comprising obtaining a serum sample from a patient who has not been previously administered the cancer vaccine; assaying the serum sample to determine the levels of antibodies in the patient to at least one glycan and/or glycoprotein antigen selected from the group consisting of Sialylα2-6Galβ1-4Glc-(6'SLac), Sialylα2-3Galβ1-4(Fucα1-3)GlcNAc-(SLeX), Sialylα2-3Galβ1-4Glc-(GM3), Fucα1-2Galβ1-3GlcNAcβ1-3Galβ1-4Glcβ-(BG-H1), GalNAcβ1-4Galβ-(GA2$_{di}$), Galβ1-4GlcNAcβ1-6(Galβ1-4GlcNAcβ1-3)Galβ-(LNnH), Galα1-3Gal-(B$_{di}$), Ac-Ser-(GalNAcα)Thr-Gly-Gly-(Ac-S-Tn(Thr)-G-G), BSM, Lactose, Galβ1-3GlcNAcβ1-3Galβ-(LNT), Fuc-b, Fuc-a, Galβ1-6Man-α-(Galb1-6Man-a), Galβ1-3GalNAcβ1-4Galβ1-(GA1), Galα1-4Galβ-(Galα1-4Galb), Manα1-6[Manα1-3]Manβ-(ManT), Galβ1-3GlcNAcβ1-3Galβ1-4GlcNAcβ1-3Galβ1-(pLNH), Rha-α-, GalNAcα1-3Galβ-(A$_{di}$), GalNAcα1-3 (Fucα1-2)Galβ-(BG-A), Galβ1-3GalNAcβ1-4Galβ1-(GA1), fetuin, and Ac-Ser-(GalNAcα)Ser-Ser-Gly-(Ac-S-Tn(Ser)-S-G); and comparing the determined levels of antibodies to the at least one glycan and/or glycoprotein antigen to a control, so as to predict the clinical response to the cancer vaccine in the patient.

The invention provides a method for determining the immune response to a cancer vaccine in a patient having cancer comprising obtaining a first serum sample from a patient who has not been previously administered the cancer vaccine; obtaining a second serum sample from the patient after administration of the cancer vaccine, assaying the first and second serum samples to determine the first and second levels of antibodies, respectively, to at least one glycan and/or glycoprotein antigen selected from the group consisting of the Forssman antigen (e.g., the Forssman disaccharide), GalNAcα1-3Galβ-(A$_{di}$), GalNAcα1-3(Fucα1-2)Galβ-(BG-A), the Tn antigen, the TF antigen, Sialylα2-3Galβ1-4(Fucα1-3)GlcNAc-(SLeX), Siaα2-3Galβ1-3 [Fucα1-4]GlcNAcβ1-(SLeA), Fucα1-2Galβ1-4(Fucα1-3) GlcNAc-(LeY), Sialylα2-6Galβ1-4Glc-(6'SLac), Sialylα2-3Galβ1-4Glc-(GM3), Fucα1-2Galβ1-3GlcNAcβ1-3Galβ1-4Glcβ-(BG-H1), GalNAcβ1-4Galβ-(GA2$_{di}$), Galβ1-4GlcNAcβ1-6(Galβ1-4GlcNAcβ1-3)Galβ-(LNnH), Galα1-3Gal-(B$_{di}$), GalNAcα1-3(Fucα1-2)Galβ1-3(Fucα1-4) GlcNAcβ1-3Galβ1-(A-LeB), and fetuin; and comparing the determined first and second levels of antibodies to the at least one glycan and/or glycoprotein antigen, so as to determine the immune response to the cancer vaccine in the patient.

The invention provides a method for predicting the clinical response to a cancer vaccine in a patient having cancer comprising obtaining a serum sample from a patient who has been previously administered the cancer vaccine; assaying the serum sample to determine the levels of antibodies in the patient to at least one glycan and/or glycoprotein antigen selected from the group consisting of the Forssman antigen (e.g., the Forssman disaccharide), GalNAcα1-3Galβ-(A$_{di}$), GalNAcα1-3(Fucα1-2)Galβ-(BG-A), fetuin, Ac-Ser-(GalNAcα)Ser-Ser-Gly-, Sialylα2-6Galβ1-4Glc-(6'SLac), Sialylα2-3Galβ1-4Glc-(GM3), Fuc-a, and GalNAcα1-3 (Fucα1-2)Galβ1-3 (Fucα1-4)GlcNAcβ1-3 Galβ1-(A-LeB); and comparing the determined levels of antibodies to the at least one glycan and/or glycoprotein antigen to a control, so as to predict the clinical response to the cancer vaccine in the patient.

The invention also provides a method for predicting long-term survival in a patient having cancer comprising obtaining a serum sample from a patient which has not been previously administered cancer treatment; assaying the serum sample to determine the levels of antibodies in the patient to at least one glycan and/or glycoprotein antigen selected from the group consisting of GalNAcβ1-4Galβ-(GA2$_{di}$-), Galβ1-4GlcNAcβ1-6(Galβ1-4GlcNAcβ1-3) Galβ-(LNnH), Sialylα2-3Galβ1-4(Fucα1-3)GlcNAc-(SLeX), Ac-Ser-(GalNAcα)Thr-Gly-Gly-(Ac-S-Tn(Thr)-G-G), Fuc-a, Fuc-b, Galβ1-3GalNAcβ1-4Galβ1-(GA1), Galβ1-6Man-α-(Galb1-6Man-a), Galα1-4Galβ-(Gala1-4Galb), Manα1-6[Manα1-3]Manβ-(ManT), Man-α (Man-a), Glcα1-6Glcβ-(isomaltose), Araα1-5Araα1-5Araα1-5Araα1-5Araα1-(Ara5), Manα1-2Manα1-6(Manα1-2Manα1-3)Manα1-6(Manα1-2Manα1- 2Manα1-3)Manβ1-4GlcNAc-(Man9), GalNAc-β (GalNAc-b), Fucα1-2Galβ1-4GlcNAcβ-(BG-H2), Galβ1-4GlcNAcβ1-3Galβ1-4GlcNAcβ1-3Galβ1-4GlcNAcβ-(LacNAc (trimeric)), Galα1-4Galβ1-4Glc-(Pk or Gb3), Glcβ1-4Glcβ-(cellobiose), Galβ1-4GlcNAcβ1-3Galβ1 (LNnT), Manα1-6Man-α

(Manα1-6Man-a) Galα1-3Galβ1-4Galα-(Gal3), Galβ1-3 (Siaα2-6)GlcNAcβ1-3Galβ1-(LSTb), GalNAc-α-(GalNAc-a), Galβ1-3(Fucα1-4)GlcNAcβ1-3Galβ1-4(Fucα1-3) GlcNAcβ1-3Galβ1-(LeA-LeX), Forssman antigen, and Ac(Galβ1-3GalNAcα)Ser-Gly-(Ac-TF(Ser)-G); and comparing the determined levels of antibodies to the at least one glycan and/or glycoprotein antigen to a control, so as to predict the long-term survival in the patient.

Additionally, the invention provides a kit for predicting the clinical response to a cancer vaccine in a patient sample from a patient having prostate cancer comprising a composition including at least one glycan and/or glycoprotein antigen selected from the group consisting of Sialylα2-6Galβ1-4Glc-(6'SLac), Sialylα2-3Galβ1-4(Fucα1-3)Glc-NAc-(SLeX), Sialylα2-3Galβ1-4Glc-(GM3), Fucα1-2Galβ1-3GlcNAcβ1-3Galβ1-4Glcβ-(BG-H1), GalNAcβ1-4Galβ-(GA2$_{di}$), Galβ1-4GlcNAcβ1-6(Galβ1-4GlcNAcβ1-3)Galβ-(LNnH), Galα1-3Gal-(B$_{di}$), Ac-Ser-(GalNAcα)Thr-Gly-Gly-(Ac-S-Tn(Thr)-G-G), BSM, Lactose, Galβ1-3GlcNAcβ1-3Galβ-(LNT), Fuc-b, Fuc-a, Galβ1-6Man-α-(Galβ1-6Man-a), Galβ1-3GalNAcβ1-4Galβ1-(GA1), Galα1-4Galβ-(Galα1-4Galb), Manα1-6[Manα1-3]Manβ-(ManT), Galβ1-3GlcNAcβ1-3Galβ1-4GlcNAcβ1-3Galβ1-(pLNH), Rha-α-, GalNAcα1-3Galβ-(A$_{di}$), GalNAcα1-3(Fucα1-2)Galβ-(BG-A), Galβ1-3GalNAcβ1-4Galβ1-(GA1), fetuin, and Ac-Ser-(GalNAcα)Ser-Ser-Gly-(Ac-S-Tn(Ser)-S-G).

The invention provides kit for determining the immune response to a cancer vaccine in a patient sample from a patient having prostate cancer comprising a composition including at least one glycan and/or glycoprotein antigen selected from the group consisting of the Forssman antigen (e.g., the Forssman disaccharide), GalNAcα1-3Galβ-(A$_{di}$), GalNAcα1-3(Fucα1-2)Galβ-(BG-A), the Tn antigen, the TF antigen, Sialylα2-3Galβ1-4(Fucα1-3)GlcNAc-(SLeX), Siaα2-3Galβ1-3[Fucα1-4]GlcNAcβ1-(SLeA), Fucα1-2Galβ1-4(Fucα1-3)GlcNAc-(LeY), Sialylα2-6Galβ1-4Glc-(6'SLac), Sialylα2-3Galβ1-4Glc-(GM3), Fucα1-2Galβ1-3GlcNAcβ1-3Galβ1-4Glcβ-(BG-H1), GalNAcβ1-4Galβ-(GA2$_{di}$), Galβ1-4GlcNAcβ1-6(Galβ1-4GlcNAcβ1-3)Galβ-(LNnH), Galα1-3Gal-(B$_{di}$), GalNAcα1-3(Fucα1-2)Galβ1-3(Fucα1-4)GlcNAcβ1-3Galβ1-(A-LeB), and fetuin.

Additionally, the invention provides a kit for predicting the clinical response to a cancer vaccine in a patient sample from a patient having prostate cancer comprising a composition including at least one glycan and/or glycoprotein antigen selected from the group consisting of the Forssman antigen (e.g., the Forssman disaccharide), GalNAcα1-3Galβ-(A$_{di}$), GalNAcα1-3(Fucα1-2)Galβ-(BG-A), fetuin, Ac-Ser-(GalNAcα)Ser-Ser-Gly-, Sialylα2-6Galβ1-4Glc-(6'SLac), Sialylα2-3Galβ1-4Glc-(GM3), Fuc-a, and GalNAcα1-3(Fucα1-2)Galβ1-3(Fucα1-4)GlcNAcβ1-3Galβ1-(A-LeB).

The invention also provides kit for predicting the long-term survival in a patient sample from a patient having prostate cancer comprising a composition including at least one glycan and/or glycoprotein antigen selected from the group consisting of GalNAcβ1-4Galβ-(GA2$_{di}$-), Galβ1-4GlcNAcβ1-6(Galβ1-4GlcNAcβ1-3)Galβ-(LNnH), Sialylα2-3Galβ1-4(Fucα1-3)GlcNAc-(SLeX), Ac-Ser-(GalNAcα)Thr-Gly-Gly-(Ac-S-Tn(Thr)-G-G), Fuc-a, Fuc-b, Galβ1-3GalNAcβ1-4Galβ1-(GA1), Galβ1-6Man-α-(Galb1-6Man-a), Galα1-4Galβ-(Galα1-4Galb), Manα1-6[Manα1-3]Manβ-(ManT), Man-α (Man-a), Glcα1-6Glcβ-(isomaltose), Araα1-5Araα1-5Araα1-5Araα1-5Araα1-(Ara5), Manα1-2Manα1-6(Manα1-2Manα1-3)Manα1-6(Manα1-2Manα1-2Manα1-3)Manβ1-4GlcNAc-(Man9), GalNAc-β(GalNAc-b), Fucα1-2Galβ1-4GlcNAcβ-(BG-H2), Galβ1-4GlcNAcβ1-3Galβ1-4GlcNAcβ1-3Galβ1-4GlcNAcβ-(LacNAc (trimeric)), Galα1-4Galβ1-4Glc-(Pk or Gb3), Glcβ1-4Glcβ-(cellobiose), Galβ1-4GlcNAcβ1-3Galβ1 (LNnT), Manα1-6Man-α (Manα1-6Man-a) Galα1-3Galβ1-4Galα-(Gal3), Galβ1-3(Siaα2-6)GlcNAcβ1-3Galβ1-(LSTb), GalNAc-α-(GalNAc-a), Galβ1-3(Fucα1-4)GlcNAcβ1-3Galβ1-4(Fucα1-3)GlcNAcβ1-3Galβ1-(LeA-LeX), Forssman antigen, and Ac(Galβ1-3GalNAcα)Ser-Gly-(Ac-TF(Ser)-G).

The invention provides a method for improving the efficacy of a virus-based vaccine in a patient comprising enhancing antibody responses to one or more glycans or glycoprotein antigens.

The invention provides a method for improving the efficacy of a virus-based vaccine in a patient comprising altering levels of antibodies in the patient prior to vaccine therapy.

The invention provides a method for improving the efficacy of a virus-based vaccine in a patient comprising increasing the amounts of one or more glycans or glycoprotein antigens in the patient.

BRIEF DESCRIPTION OF THE SEVERAL VIEWS OF THE DRAWING(S)

FIGS. 1A-D are Kaplan-Meier curves comparing survival of patients with pre-vaccination antibody levels above or below the cutoff for Sialyl LeX (cutoff=9.6, p=0.0002, FIG. 1A), BG-H1 (cutoff=13.2; p=0.0001; FIG. 1B), B$_{di}$ (cutoff=14.2; p=0.0005; FIG. 1C), and BG-A (IgM cutoff=11.4; p=0.0001; FIG. 1D). All are at a dilution of 1:50. In FIGS. 1A and 1B, the survival of patients above cutoff is represented by the lower (solid) line and the survival of patients below cutoff is represented by the upper (dotted) line. In FIGS. 1C and 1D, the survival of patients about cutoff is represented by the upper (dotted) line and the survival of patients below cutoff is represented by the lower (solid) line.

FIG. 2 contains a list of selected array components and the structures of selected linkers. The array components allow the detection of the relevant subpopulations of serum antibodies, which can serve as biomarkers.

DETAILED DESCRIPTION OF THE INVENTION

Antibodies are a critical element of the immune response. Although there is good agreement that antibody responses are vital for many vaccines targeting pathogens, the role of antibody responses for cancer vaccines is still a matter of debate. Numerous studies show that antibodies can affect the outcome, but the response can either be beneficial or detrimental. The effect is likely to depend on many factors, such as the antibody isotype and subclass, target antigen, affinity, and selectivity.

A number of studies show that induction of antibodies by cancer vaccines correlates with improved survival. In addition, there is evidence that these antibodies can directly contribute to anti-tumor immunity by binding and killing tumor cells, a process that could be especially important for preventing metastases. Other studies suggest that antibody responses can be unfavorable. In some cases, antibodies can enhance growth of tumors and protect cells from killing by cytotoxic T lymphocytes (CTL). In certain mouse cancer model studies, removal of B cells has been shown to reduce tumor burden and enhance effectiveness of cancer vaccines.

Antibodies to glycans also can influence the response to vaccines. Using pre-clinical models, Stager et al., *Nat. Med.*, 9: 1287-1292 (2003) showed that natural antibodies help stimulate favorable immune responses to vaccines. Since anti-glycan antibodies are a major class of natural antibodies, pre-existing anti-glycan antibodies could influence immune responses to vaccines. Moreover, individuals with widely different levels of some anti-glycan antibodies could mount very different immune responses to the same vaccine. For these reasons, additional studies are needed to fully understand the role of antibodies for cancer vaccines.

Carbohydrate antigens are directly or indirectly involved in most types of cancer vaccines, but this class of antigens has been largely understudied. Some vaccines specifically target tumor-associated carbohydrate antigens. For example, a number of vaccines targeting tumor-associated carbohydrate antigens, such as Tn, TF, sialyl-Tn, and Globo H, have been prepared and evaluated (see, e.g., Keding et al., *Proc. Natl. Acad. Sci. USA,* 101(33): 11937-11942 (2004)). For these vaccines, a key question is whether a given patient expresses the target antigen.

Glycans also can be involved in other vaccines that do not specifically target a carbohydrate antigen. For example, cells display an abundance of glycans on their cell surface, and the glycan content changes significantly with the onset and progression of cancer. Therefore, vaccines based on whole tumor cells present a variety of carbohydrate antigens to the immune system, many of which are not normally present in healthy tissue.

Vaccines based on specific proteins also can involve carbohydrates, since many of them are post-translationally modified with glycans. Glycans can even play a role in vaccines that do not directly contain carbohydrate antigens. An immune response to a specific antigen on a target cell can lead to a process referred to as "antigen spreading" or "antigen cascade" (see, e.g., Ranieri et al., *Immunol. Invest.,* 29(2): 121-125 (2000), Disis et al., *J. Clin. Oncol.,* 20(11): 2624-2632 (2002), Butterfield et al., *Clin. Cancer Res.,* 9(3): 998-1008 (2003), Wierecky et al., *Cancer Immunol. Immunother.,* 55(1): 63-67 (2006), and Arlen et al., *Clin. Cancer Res.,* 12(4): 1260-1269 (2006)). As cells are killed, presentation of other cellular components can lead to a broader immune response against antigens that were not present in the original vaccine. Antigen cascade is associated with more potent immune responses and better clinical outcomes. Carbohydrates are an abundant family of antigens found on tumor cells, but it is not presently known if antigen spreading to glycans occurs after vaccination, nor is it known if antigen spreading to glycans is beneficial for clinical outcomes.

Through direct and/or indirect mechanisms, there are numerous glycans that could be involved in the immune response induced by a vaccine, such as a cancer vaccine. It is extremely difficult to predict which glycans will be targeted.

Accordingly, the invention provides a method for predicting the clinical (immune) response to a cancer vaccine in a patient having cancer. The method comprises obtaining a serum sample from the patient prior to the administration of the vaccine to the patient, assaying the serum sample to determine the levels of antibodies in the patient to at least one glycan and/or glycoprotein antigen, and comparing the determined levels of antibodies to the at least one glycan and/or glycoprotein antigen to a control, so as to predict the clinical response to the cancer vaccine in the patient.

Additionally, the invention provides a method of predicting long-term survival in a patient having cancer comprising obtaining a serum sample from a patient who has not received cancer treatment (e.g., administration of a cancer vaccine), assaying the serum from the patient for antibody levels to at least one glycan and/or glycoprotein antigen, and comparing the determined levels of antibodies to the at least one glycan and/or glycoprotein antigen to a control, so as to predict the long-term survival in the patient (e.g., in response to cancer treatment).

The methods to determine the immune response to these antigens can be used to predict which patients will have a clinical benefit from the vaccine. Once the antibody response to these antigens is determined and compared to a control, the antibody response can be used as an early indicator of a beneficial response, an early indicator of efficacy, or an early indicator of a favorable (or unfavorable) response.

The term "antibody" refers to a specific protein binding partner for an antigen and is any substance, or group of substances, which has a specific binding affinity for an antigen to the exclusion of other substances. The generic term antibody includes polyclonal antibodies, monoclonal antibodies, and antibody fragments. Specific classes of antibodies include, but are not limited to, IgG, IgM, IgA, IgD, and IgE. The levels of antibodies measured can be from only one class of antibody (e.g., IgG, IgM, IgA, IgD, or IgE) or combinations thereof (e.g., two or more classes of antibodies, three or more classes of antibodies, four or more classes of antibodies, or five or more classes of antibodies). For example, the antibody levels of IgG, IgM, and IgA collectively (anti-Ig) can be measured. Alternatively, the ratios of antibodies, such as IgA/IgM or (IgA+IgG)/IgM, can be measured.

The levels of antibodies can be measured at any serum dilution. For example, serum dilutions of 1:10, 1:25, 1:30, 1:50, 1:100, 1:200, 1:250, 1:300, 1:400, and 1:500 can be used in the inventive methods.

Detection of antibodies from the patient samples can be accomplished using techniques known in the art, such as immunoenzymatic techniques, e.g., immunoperoxidase staining technique, or the avidin-biotin technique, or immunofluorescence techniques (see, e.g., Ciocca et al., *Meth. Enzymol.,* 121:562-79 (1986), and *Introduction to Immunology*, ($2^{nd}$ Ed), 113-117, Macmillan Publishing Company (1986)). Serologic diagnostic techniques involve the detection and quantification of other associated antigens that have been secreted or "shed" into the serum or other biological fluids of patients. Such antigens can be detected in the biological fluids using techniques known in the art, such as radioimmunoassays (RIA) or enzyme-linked immunoabsorbent assays (ELISA), wherein antibody reactive with the shed antigen is used to detect the presence of the antigen in a fluid sample (See, e.g., Uotila et al., *J. Immunol. Methods,* 42: 11 (1981) and Fayed et al., *Disease Markers,* 14: 155-160 (1998)).

The patient can be a mammal, such as a mouse, rat, hamster, guinea pig, rabbit, cat, dog, pig, cow, horse, or primate. Preferably, the patient is human.

The cancer of the patient is not particularly limited. Examples include prostate, breast, pancreatic, ovarian, gastric, head and neck, liver, lung, kidney, bone, brain, colorectal, uterine, skin, endometrial, esophageal, anal, oral, nasal, and rectal cancers. Preferably, the cancer of the patient is prostate cancer.

The cancer vaccine can be any potential cancer vaccine. Examples include, but are not limited to, prostate cancer vaccines, breast cancer vaccines, pancreatic cancer vaccines, ovarian cancer vaccines, gastric cancer vaccines, head and neck cancer vaccines, liver cancer vaccines, lung cancer vaccines, kidney cancer vaccines, bone cancer vaccines, brain cancer vaccines, colorectal cancer vaccines, uterine cancer vaccines, skin cancer vaccines, endometrial cancer vaccines, esophageal cancer vaccines, anal cancer vaccines, oral cancer vaccines, nasal cancer vaccines, and rectal cancer vaccines.

The vaccine can be a peptide-based, plasmid-based, or viral vector-based vaccine. Viral vector-based vaccines include, but are not limited to, poxvirus-based, adenovirus-based, and adeno-associated virus-based vaccines. When the vaccine is a poxvirus-based vaccine, the poxvirus can be any suitable poxvirus, such as avipox (e.g., fowlpox, canarypox, and pigeonpox) or orthopox (vaccinia (e.g., MVA and NYVAC), cowpox, camelpox, and monkeypox). Preferably, the cancer vaccine is a prostate cancer poxvirus-based vaccine, such as PROSTVAC-VF.

PROSTVAC-VF is composed of an initial vaccination with a recombinant vaccinia virus containing the human genes for prostate specific antigen (PSA) and three costimulatory molecules (B7.1, LFA-3, and ICAM-1), followed by booster injections with a fowlpox virus with the same four transgenes (see, e.g., Garnett et al., *Curr. Pharm. Des.*, 12: 351-361 (2006), and Madan et al., *Expert Opin. Biol. Ther.*, 10: 19-28 (2010)). The vaccine is designed to stimulate an immune response to prostate tumor cells that express high levels of PSA. The vaccine has been evaluated in several phase I and phase II clinical trials with excellent results (see, e.g., Gulley et al., *Cancer Immunol. Immunother.*, 2(2): 155-158 (2010), Lechleider et al., *Clin. Cancer Res.*, 14: 5284-5291 (2008), Madan et al., *Clin. Cancer Res.*, 14: 4526-4531 (2008), Garnett et al., *Clin. Cancer Res.*, 14: 3536-3544 (2008), Arlen et al., *J. Urol.*, 178:1515-1520 (2007), Theoret et al., *Clin. Genitourin. Cancer*, 5: 347-350 (2007), and Arlen et al., *Clin. Cancer Res.*, 12: 1260-1269 (2006)).

The number of glycan and/or glycoprotein antigens assayed can be any suitable number (e.g., one, two, three, four, five, six, seven, eight, nine, ten, or more). Preferably, the number of glycan and/or glycoprotein antigens assayed is at least two (e.g., at least three, at least four, at least five, at least six, at least seven, at least eight, at least nine, or at least ten).

The glycan and/or glycoprotein antigens for use in the inventive methods and kits can be presented on an antigen surface, such as an array (e.g., a glycan array as described in Example 1 and Oyelaran et al., *J. Proteome Res.*, 8: 3529-3538 (2009)).

It is known in the art that multivalent binding is important for antibody recognition of glycans. Therefore, the glycans and/or glycoproteins can be attached (e.g., conjugated) to carrier molecules (scaffolds), such as proteins, dendrimers, nanoparticles, liposomes, and certain biocompatible polymers known to those in the art. Preferably, the glycans are attached to a protein, such as bovine serum albumin (BSA) or human serum albumin (HSA).

It is also known in the art that the spacing and orientation of antigens and their epitopes are important for antibody recognition and the formation of multivalent interactions. Therefore, the glycans can be attached to the carrier molecules in varying amounts to produce conjugates with varying glycan densities. For example, the number of glycans attached to each carrier molecule (e.g., albumin, such as BSA) can be modulated to produce glycan-carrier conjugates (e.g., glycoproteins) with varying densities. When these conjugates are immobilized on a surface, the surface will display varying glycan densities. Conjugation ratios for the carrier molecules, such as albumin, can be as little as zero (i.e., no addition of carrier molecules) or fifty or more (i.e., for every carrier molecule, there are fifty glycan molecules). Exemplary conjugation ratios include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Alternatively, the density of glycan-carrier conjugates can be varied by mixing unmodified carrier molecules with the glycan and/or glycoprotein antigens and immobilizing the mixture on a surface. For example, the glycan and/or glycoprotein antigens can be mixed with differing amounts of albumin (e.g., BSA or HSA) and added to a surface (e.g., an array surface). As the proportion of the albumin increases, the glycan and/or glycoprotein antigens become further spaced apart on the surface. The larger the amount of albumin, the lower the density of the glycan and/or glycoprotein antigens on the surface (see, e.g., Zhang et al., *Mol. Biosyst.*, 6: 1-9 (2010)).

In another embodiment, the glycans (e.g., oligosaccharide lactols) and/or glycoproteins can be attached directly to an antigen surface using a hydrazide, hydrazine, amino-, or aminoxy modified surface, or can incorporate other linkers with an appropriate functional group for attaching to a surface.

Linkers for use in the inventive methods and kits include, but are not limited to Hex, CETE, APE, APD, and MEAG (see FIG. 2); however, other molecules can be used, including other organic molecules, polypeptides, or polymers known to those in the art.

The glycan and/or glycoprotein antigens for use in the inventive methods and kits include, but are not limited to, those listed in FIG. 2. In particular, the glycan and/or glycoprotein antigens can be selected from the group consisting of Sialylα2-6Galβ1-4Glc-(6'SLac), Sialylα2-3Galβ1-4(Fucα1-3)GlcNAc-(SLeX), Sialylα2-3Galβ1-4Glc-(GM3), Fucα1-2Galβ1-3GlcNAcβ1-3Galβ1-4Glcβ-(BG-H1), GalNAcβ1-4Galβ-(GA2$_{di}$), Galβ1-4GlcNAcβ1-6(Galβ1-4GlcNAcβ1-3)Galβ-(LNnH), Galα1-3Gal-(B$_{di}$), Ac-Ser-(GalNAcα)Thr-Gly-Gly-(Ac-S-Tn(Thr)-G-G), bovine submaxillary mucin (BSM), Lactose, Galβ1-3GlcNAcβ1-3Galβ-(LNT), Fuc-b, Fuc-a, Galβ1-6Man-α (Galb1-6Man-a), Galβ1-3GalNAcβ1-4Galβ1-(GA1), Galα1-4Galβ-(Gala1-4Galb), Manα1-6[Manα1-3]Manβ-(ManT), Galβ1-3GlcNAcβ1-3Galβ1-4GlcNAcβ1-3Galβ1-(pLNH), the Forssman antigen (e.g., the Forssman disaccharide, GalNAcα1-3GalNAcβ1-), GalNAcα1-3Galβ-(A$_{di}$), GalNAcα1-3(Fucα1-2)Galβ-(BG-A), the Tn antigen, the TF antigen, Siaα2-3Galβ1-3[Fucα1-4]GlcNAcβ1-(SLeA), Fucα1-2Galβ1-4(Fucα1-3)GlcNAc-(LeY), Man-α (Man-a), Glcα1-6Glcβ-(isomaltose), Araα1-5Araα1-5Araα1-5Araα1-5Araα1(Ara5), Manα1-2Manα1-6(Manα1-2Manα1-3)Manα1-6(Manα1-2Manα1-2Manα1-3)Manβ1-4GlcNAc-(Man9), GalNAc-β-(GalNAc-b), Fucα1-2Galβ1-4GlcNAcβ-(BG-H2), Galβ1-4GlcNAcβ1-3Galβ1-4GlcNAcβ1-3Galβ1-4GlcNAcβ-(LacNAc (trimeric)), Galα1-4Galβ1-4Glc-(Pk or Gb3), Glcβ1-4Glcβ-(cellobiose), Galβ1-4GlcNAcβ1-3Galβ1(LNnT), Manα1-6Man-α (Manα1-6Man-a)Galα1-3Galβ1-4Galα-(Gal3), Galβ1-3(Siaα2-6)GlcNAcβ1-3Galβ1-(LSTb), GalNAc-α-(GalNAc-a), Galβ1-3(Fucα1-4)GlcNAcβ1-3Galβ1-4(Fucα1-3)GlcNAcβ1-3Galβ1-(LeA-LeX), Rha-α, fetuin, Ac-Ser-(GalNAcα)Ser-Ser-Gly-(Ac-S-Tn(Ser)-S-G), and Ac(Galβ1-3GalNAcα)Ser-Ser-Gly-(Ac-TF(Ser)-G), and GalNAcα1-3(Fucα1-2)Galβ1-3(Fucα1-4)GlcNAcβ1-3Galβ1-(A-LeB). Additionally, encompassed by the invention are fragments or substructures of these glycans and/or glycoprotein antigens, as well larger glycans and/or glycoprotein antigens that include these structures as fragments. For example, LNnH is a hexasaccharide; however, fragments of the full hexasaccharide (e.g., tetrasaccharide and pentasaccharide) also are encompassed by the invention. Furthermore, Rha-α is a monosaccharide and other glycans that comprise this monosaccharide as a terminal structure are encompassed by the invention.

A preferred example of the glycan and/or glycoprotein antigens for use in the inventive methods and kits is the Forssman antigen. As used herein, the term "Forssman antigen" encompasses the full pentasaccharide, as well as the trisaccharide, tetrasaccharide, or the disaccharide discussed above (i.e., fragments or substructures of the full pentasaccharide). In addition, it encompasses longer oligosaccharides or polysaccharides that contain a Forssman antigen.

The invention also encompasses glycan and/or glycoprotein antigens that are similar in structure to the Forssman antigen. An example is the "core 5" glycan (GalNAcα1-3GalNAcα1-) that is very close in structure to the Forssman disaccharide (GalNAcα1-3GalNAcβ1-). Core 5 glycan alternatively could be used to detect anti-Forssman antibodies, since core 5 glycan is similar in structure and has cross-reactivity.

Another preferred example of the glycan and/or glycoprotein antigens for use in the inventive methods and kits is the blood group A antigen (BG-A). As used herein, the term "BG-A" encompasses the trisaccharide as well as other oligosaccharides or polysaccharides that contain the blood group A trisaccharide as a substructure.

Exemplary embodiments of glycan and/or glycoprotein antigens for use in the inventive methods and kits, which antigens are attached to linkers and/or carrier molecules (e.g., BSA), include, but are not limited to, GalNAcβ1-4Galβ-(37/BSA) ($GA2_{di}$-37), Galβ1-4GlcNAcβ1-6(Galβ1-4GlcNAcβ1-3)Galβ-(11/BSA) (LNnH-11), Ac-Ser-(GalNAcα)Thr-Gly-Gly-Hex-(7/BSA) (Ac-S-Tn(Thr)-G-G-07), Ac-Ser-(GalNAcα)Thr-Gly-Gly-Hex-(24/BSA) (Ac-S-Tn(Thr)-G-G-24), Galβ1-3GlcNAcβ1-3Galβ-(5/BSA) (LNT-05), Fuc-b-(4/BSA) (Fuc-b-04), Fuc-b-(22/BSA) (Fuc-b-22), Fuc-a-(4/BSA) (Fuc-a-04), Fuc-a-(22/BSA) (Fuc-a-22), Galβ1-3GalNAcβ1-4Galβ1-(6/BSA) (GA1-06), Galβ1-3GalNAcβ1-4Galβ1-(20/BSA) (GA1-20), Galβ1-3GlcNAcβ1-3Galβ1-4GlcNAcβ1-3Galβ1-(7/BSA) (pLNH-07), GalNAcα1-3GalNAcβ1-(4/BSA) (Forssman di-04), GalNAcα1-3GalNAcβ1-21/BSA) (Forssman di-21), GalNAcα1-3GalNAcβ1-(31/BSA) (Forssman di-31), and GalNAc-α-BSA (4/BSA) (GalNAc-a-04), GalNAc-α-BSA (22/BSA) (GalNAc-a-22), Galβ1-4GlcNAcβ1-3Galβ1-BSA (14/BSA) (LNnt-14), GalNAcα1-3Galβ-(4/BSA) ($A_{di}$-04), GalNAcα1-3Galβ-(17/BSA) ($A_{di}$-17), Ac-Ser-(GalNAcα) Ser-Ser-Gly-Hex-(4/BSA) (Ac-S-Tn(Ser)-S-G-04), Ac-Ser-(GalNAcα)Ser-Ser-Gly-Hex-(22/BSA) (Ac-S-Tn(Ser)-S-G-22), Ac-Ser-(GalNAcα)Ser-Ser-Gly-Hex-(33/BSA) (Ac-S-Tn(Ser)-S-G-33), Ac(Galβ1-3GalNAcα)Ser-Gly-Hex-(4/BSA) (Ac-TF(Ser)-G-04), Ac(Galβ1-3GalNAcα)Ser-Gly-Hex-(24/BSA) (Ac-TF(Ser)-G-24), Rha-1-BSA, ManT-BSA, BG-A, fetuin, and A-LeB. Carrier molecules, such as proteins (e.g., BSA and HSA), dendrimers, nanoparticles, liposomes, and biocompatible polymers can be used.

In one embodiment, a method is provided for predicting the clinical (immune) response to a cancer vaccine in a patient having cancer comprising obtaining a serum sample from a patient who has not been previously administered the cancer vaccine; assaying the serum sample to determine the levels of antibodies in the patient to at least one glycan and/or glycoprotein antigen selected from the group consisting of 6'SLac, SLeX, GM3, BG-H1, $GA2_{di}$, LNnH, $B_{di}$, Ac-S-Tn(Thr)-G-G, BSM, Lactose, LNT, Fuc-b, Fuc-a, Galb1-6Man-a, GA1, Gala1-4Galb, ManT, pLNH, Rha-α, $A_{di}$, BG-A, GA1, fetuin, and Ac-S-Tn(Ser)-S-G; and comparing the determined levels of antibodies to the at least one glycan and/or glycoprotein antigen to a control, so as to predict the immune response to the cancer vaccine in the patient. Such a method can be used to predict whether a patient will have a positive response to treatment with a vaccine (e.g., cancer vaccine).

Preferably, this method comprises determining the levels of antibodies in the patient to at least one glycan and/or glycoprotein antigen selected from the group consisting of 6'SLac, GM3, LNnH, Fuc-a, Rha-α, $A_{di}$, BG-A, GA1, fetuin, and Ac-S-Tn(Ser)-S-G, as well as fragments or substructures of these glycans and/or glycoprotein antigens and larger glycans and/or glycoprotein antigens that include these structures as fragments.

Most preferably, the levels of IgM antibodies to blood group A or a derivative of blood group A (BG-A) are assayed. Additionally or alternatively, the levels of IgG antibodies to GA1, the levels of IgG antibodies to Rha-α, the levels of IgA antibodies to Fuc-a, the levels of Ig antibodies to LNnH, the levels of IgG antibodies to 6'SLac, and/or the levels of IgG antibodies to GM3 are measured.

In another embodiment, a method is provided for determining the immune response to a cancer vaccine in a patient having cancer comprising obtaining a first serum sample from a patient who has not been previously administered the cancer vaccine; obtaining a second serum sample from the patient after administration of the cancer vaccine, assaying the first and second serum samples to determine the first and second levels of antibodies, respectively, to at least one glycan and/or glycoprotein antigen selected from the group consisting of Forssman antigen (e.g., Forssman disaccharide or an antigen similar in structure to the Forssman antigen, such as core 5), $A_{di}$, BG-A, the Tn antigen, the TF antigen, SLeX, SLeA, LeY, 6'SLac, GM3, BG-H1, $GA2_{di}$, LNnH, $B_{di}$, A-LeB, and fetuin; and comparing the determined first and second levels of antibodies to the at least one glycan and/or glycoprotein antigen, so as to determine the immune response to the cancer vaccine in the patient. Such a method can be used to determine whether a patient will clinically benefit from administration of the vaccine.

Preferably, this method comprises determining the levels of antibodies to at least one glycan and/or glycoprotein antigen selected from the group consisting of Forssman antigen, core 5, A-LeB, $A_{di}$, BG-A, and fetuin, as well as fragments or substructures of these glycans and/or glycoprotein antigens and larger glycans and/or glycoprotein antigens that include these structures as fragments.

Most preferably, this method comprises determining the levels of IgA or Ig antibodies to the Forssman antigen (e.g., Forssman disaccharide or an antigen similar in structure to the Forssman antigen, such as core 5).

In another embodiment, a method is provided for predicting the clinical response to a cancer vaccine in a patient having cancer comprising obtaining a serum sample from a patient who has been previously administered the cancer vaccine (e.g., 2 months, 3 months, or 4 months post-vaccination); assaying the serum sample to determine the levels of antibodies in the patient to at least one glycan and/or glycoprotein antigen selected from the group consisting of the Forssman antigen (e.g., the Forssman disaccharide), $A_{di}$, BG-A, fetuin, Ac-Ser-(GalNAcα)Ser-Ser-Gly-, 6'SLac, GM3, Fuc-a, and A-LeB; and comparing the determined levels of antibodies to the at least one glycan and/or glycoprotein antigen to a control, so as to predict the clinical response to the cancer vaccine in the patient.

In yet another embodiment, a method is provided for predicting long-term survival in a patient having cancer comprising obtaining a serum sample from a patient which has not been previously administered cancer treatment; assaying the serum sample to determine the levels of antibodies in the patient to at least one glycan and/or glycoprotein antigen selected from the group consisting of $GA2_{di}$, LNnH, SLeX, Ac-S-Tn(Thr)-G-G, Fuc-a, Fuc-b, Galb1-6Man-a, GA1, Gala1-4Galb, ManT, Man-a, isomaltose, Ara5, Man9, GalNAc-b, BG-H2, LacNAc (trimeric), Pk or Gb3, cellobiose, LNnT, Mana1-6Man-a, Gal3, LSTb, GalNAc-a, LeA-LeX, Forssman antigen (e.g., Forssman disaccharide or an antigen similar in structure to the Forssman antigen, such as core 5), and Ac-TF(Ser)-G; and comparing the determined levels of antibodies to the at least one glycan and/or glycoprotein antigen to a control, so as to predict the long-term survival in the patient.

Preferably, this method comprises determining the levels of antibodies to at least one glycan and/or glycoprotein antigen selected from the group consisting of Galα1-4Galb, ManT, LSTb, Forssman antigen, core 5, and Ac-TF(Ser)-G, as well as fragments or substructures of these glycans and/or glycoprotein antigens and larger glycans and/or glycoprotein antigens that include these structures as fragments. Additionally or alternatively, the levels of antibodies to BS-A can be determined and compared to a control.

The control to which the levels of antibodies to a particular antigen are compared can be any suitable control. The control can be a positive or negative control. Examples of positive controls include (i) a value determined to be an average level of the antibodies to the particular antigen in the serum of patients that respond positively to the cancer vaccine (i.e., patients who exemplified a strong immune response to the cancer vaccine), (ii) a value determined to be the threshold value above or below which the patient will respond positively to the cancer vaccine, (iii) a value determined to be an average level of the antibodies to the particular antigen in the serum of patients who exhibit long-term survival, and (iv) a threshold value above or below which there is an increased likelihood that the patient will exhibit long-term survival.

Examples of negative controls include (i) a value determined to be an average level of the antibodies to the particular antigen in the serum of patients that respond negatively to the cancer vaccine (i.e., patients who exemplified little (weak) or no immune response to the cancer vaccine), (ii) a value determined to be the threshold value above or below which the patient will respond negatively to the cancer vaccine, (iii) a value determined to be an average level of the antibodies to the particular antigen in the serum of patients that do not exhibit long-term survival, and (iv) a threshold value above or below which there is an increased likelihood that the patient will not exhibit long-term survival. A threshold value can be determined by any conventional method.

A positive response to treatment (e.g., the cancer vaccine) includes, but is not limited to, an increased immune response to the cancer, a decrease in tumor size, a decrease in tumor mass, a decrease in the number of tumor cells, a decrease in metastasis, and/or increased survival.

Long-term survival refers to a survival of greater than the average survival in patients having a particular cancer (e.g., at least 6 months, at least 1 year, at least 2 years, at least 3 years, at least 4 years, at least five years, at least six years, at least seven years, at least eight years, at least nine years, at least ten years, or more when compared to the average survival in patients having a particular cancer).

When two values are being compared (e.g., the levels of antibodies to one or more antigens between a first and second serum sample), the values preferably are significantly different (e.g., statistically significant ($p \leq 0.05$)).

Kits comprising at least one (e.g., at least two, at least three, at least four, at least five, at least six, at least seven, at least eight, at least nine, at least ten, or more) glycan and/or glycoprotein antigen also is encompassed by the invention. The components in the kit can be provided in packaged combination in the same or in separate containers, depending on their cross-reactivities and stabilities. The amounts and proportions of reagents provided in the kit can be selected so as to provide optimum results for a particular application.

The kit further can comprise ligands of the analyte and calibration and control materials, and also can include antibody standards for the antigens tested. The components of the kit can be in any suitable form, such as liquid or lyophilized.

In one embodiment, a kit is provided for predicting the clinical (immune) response to a cancer vaccine in a patient sample from a patient having cancer comprising a composition including at least one or more (e.g., two, three, four, five, six, seven, eight, nine, ten, or more) glycan and/or glycoprotein antigen selected from the group consisting of: 6'SLac, SLeX, GM3, BG-H1, $GA2_{di}$, LNnH, $B_{di}$, Ac-S-Tn(Thr)-G-G, BSM, Lactose, LNT, Fuc-b, Fuc-a, Galb1-6Man-a, GA1, Gala1-4Galb, ManT, Rha-α-, $A_{di}$, BG-A, GA1, Ac-S-Tn(Ser)-S-G, fetuin, and pLNH. Such a kit can be used to predict whether a patient (from which the sample was obtained) will benefit from administration of the cancer vaccine.

In another embodiment, a kit is provided for determining the immune response to a cancer vaccine in a patient sample from a patient having cancer (e.g., prostate cancer) comprising composition including at least one (e.g., two, three, four, five, six, seven, eight, nine, ten, or more) glycan and/or glycoprotein antigen selected from the group consisting of the Forssman antigen (e.g., the Forssman disaccharide), $A_{di}$, BG-A, the Tn antigen, the TF antigen, SLeX, SLeA, LeY, 6'SLac, GM3, BG-H1, $GA2_{di}$, LNnH, $B_{di}$, A-LeB, and fetuin.

In another embodiment, a kit is provided for predicting the clinical (immune) response to a cancer vaccine in a patient sample from a patient having cancer (e.g., prostate cancer) comprising a composition including at least one glycan and/or glycoprotein antigen selected from the group consisting of the Forssman antigen (e.g., the Forssman disaccharide), GalNAcα1-3Galβ-($A_{di}$), GalNAcα1-3 (Fucα1-2)Galβ-(BG-A), fetuin, Ac-Ser-(GalNAcα)Ser-Ser-Gly-, Sialylα2-6Galβ1-4Glc-(6'SLac), Sialylα2-3Galβ1-4Glc-(GM3), Fuc-a, GalNAcα1-3 (Fucα1-2)Galβ1-3 (Fucα1-4)GlcNAcβ1-3 Galβ1-(A-LeB).

In yet another embodiment, a kit is provided for predicting the long-term survival in a patient sample from a patient having cancer (e.g., prostate cancer) comprising a composition including at least one glycan and/or glycoprotein antigen selected from the group consisting of $GA2_{di}$, LNnH, SLeX, Ac-S-Tn(Thr)-G-G, Fuc-a, Fuc-b, Galb1-6Man-a, GA1, Gala1-4Galb, ManT, Man-a, isomaltose, Ara5, Man9, GalNAc-b, BG-H2, LacNAc (trimeric), Pk or Gb3, cellobiose, LNnT, Mana1-6Man-a, Gal3, LSTb, GalNAc-a, LeA- LeX, Forssman antigen (e.g., the Forssman disaccharide), and Ac-TF(Ser)-G. Additionally or alternatively, the kit can comprise BS-Al.

The invention also includes methods for improving the efficacy of a virus-based vaccine in a patient. The method comprises enhancing antibody responses to the glycans and/or glycoprotein antigens described in connection with the inventive methods and/or stimulating responses to the particular glycans and/or glycoprotein antigens in patients (e.g., the Forssman antigen and/or BG-A).

For example, in order to improve the efficacy of a vaccine in a patient, responses to the Forssman antigen (or fragments or substructures of the Forssman antigen and larger glycans and/or glycoprotein antigens that include these structures as fragments) can be purposely enhanced and/or stimulated. Enhancing and/or stimulating response to the Forssman antigen can be done using any suitable means known in the art. For example, host cells can be genetically engineered to produce (more) Forssman antigen (e.g., Forssman disaccharide), such as by administering a vector comprising a nucleic acid sequence encoding the enzymes involved in the biosynthesis of the Forssman antigen. Tissue culture conditions can be altered to induce higher expression of the Forssman antigen, such as by supplementing the culture with GalNAc or treating the culture with a small molecule inducer of GalNAc alpha transferase. Host cell lines with enhanced production of the Forssman antigen can be identified, and the virus-based vaccine can be grown using that cell line. Forssman or Forssman-like oligosaccharides can be chemically or enzymatically added to the viral surface of the virus-based vaccine. A Forssman-containing protein, dendrimer, nanoparticle, liposome, or polymer (or other conjugate suitable for inducing antibodies) can be added as a second component of the vaccine or as a secondary injection. Additionally or alternatively, vaccination can be performed with a Forssman-containing protein, dendrimer, nanoparticle, liposome, or polymer prior to or after vaccination with the vaccine (e.g., PROSTVAC-VF or ALVAC-HIV).

The invention also includes methods for improving the efficacy of a virus-based vaccine in a patient through altering the patient's antibody populations prior to starting vaccine therapy. For example, in order to improve the efficacy of a vaccine in a patient, antibody levels to IgM in the patient could be increased by pre-vaccinating with a BG-A-containing protein, dendrimer, nanoparticle, liposome, or polymer (or other conjugate suitable for inducing antibodies).

The invention also includes methods for improving the efficacy of a virus-based vaccine by increasing the amounts of key glycans and/or glycoprotein antigens, such as BG-A and the Forssman antigen, such that pre-existing antibodies more readily recognize the virus. For example, host cells can be genetically engineered to produce (more) BG-A antigen (e.g., BG-A trisaccharide), such as by administering a vector comprising a nucleic acid sequence encoding the enzymes involved in the biosynthesis of the BG-A antigen. Tissue culture conditions can be altered to induce higher expression of the BG-A antigen. Host cell lines with enhanced production of the BG-A antigen can be identified, and the virus-based vaccine can be grown using that cell line.

The virus-based vaccine can be any suitable vaccine, including, but not limited to, poxvirus-based, adenovirus-based, and adeno-associated virus-based vaccines. Preferably, the vaccine is a poxvirus-based vaccine, such as a vaccine based on avipox (e.g., fowlpox, canarypox, and pigeonpox) or orthopox (vaccinia (e.g., MVA and NYVAC), cowpox, camelpox, and monkeypox) viruses.

The vaccine can be used for any suitable purpose and preferably is used to prevent or treat cancer or to treat or prevent infection by a virus. Examples of suitable cancer vaccines include, but are not limited to, prostate cancer vaccines, breast cancer vaccines, pancreatic cancer vaccines, ovarian cancer vaccines, gastric cancer vaccines, head and neck cancer vaccines, liver cancer vaccines, lung cancer vaccines, kidney cancer vaccines, bone cancer vaccines, brain cancer vaccines, colorectal cancer vaccines, uterine cancer vaccines, skin cancer vaccines, endometrial cancer vaccines, esophageal cancer vaccines, anal cancer vaccines, oral cancer vaccines, nasal cancer vaccines, and rectal cancer vaccines. Preferably, the cancer vaccine is a prostate cancer poxvirus-based vaccine, such as PROSTVAC-VF.

Examples of suitable vaccines against viral infection include, but are not limited to, HIV vaccines, hepatitis virus vaccines, influenza virus vaccines, HPV vaccines, and Ebola virus vaccines. Preferably, the virus vaccine is a poxvirus-based HIV vaccine, such as ALVAC-HIV (see, e.g., Kim et al., *New England Journal of Medicine*, 361: 2209-2220 (2009); Estaban, *Human Vaccines*, 5(12): 867-871 (2009); and Kaufman et al., *Expert Opinion on Biological Therapy*, 4: 575-588 (2004)).

The following examples further illustrate the invention but, of course, should not be construed as in any way limiting its scope.

EXAMPLE 1

This example demonstrates the identification of predictive markers and markers of efficacy of a clinical vaccine treatment for prostate cancer.

Initial studies were conducted on serum samples from 29 patients immunized with the PROSTVAC-VF vaccine. Briefly, patients with metastatic castrate-resistant prostate cancer were vaccinated once with a recombinant vaccinia virus containing the human genes for prostate specific antigen (PSA) and three costimulatory molecules (B7.1, LFA-3, and ICAM-1). Patients received monthly boosters with the recombinant fowlpox virus containing the same four transgenes. Patients with a rising PSA or new lesions were taken off study for disease progression, but survival status was updated periodically. Sera prior to vaccination and 3 months after vaccination were profiled on a neoglycoprotein array as described in Zhang et al., *Mol. Biosyst.*, 6: 1-9 (2010). Exemplary array components are listed in FIG. 2. IgG, IgM, and IgA collectively (anti-Ig) at dilutions of 1:50 and 1:200 were measured.

Predictive Biomarkers

Predictive biomarkers are useful for tailoring treatment to individual patients. To evaluate relationships between antibody levels and survival, the Partek Genomics Suite software was used. With this software, correlations (e.g., Pearson correlation) were evaluated, hazard ratios (HR) (e.g., Cox regression) were determined, and Kaplan-Meier curves were generated.

For the majority of carbohydrate antigens, lower serum antibody levels were associated with increased survival. Tables 1 and 2 indicate the hazard ratios, Pearson correlations with overall survival, and associated p-values for the best antigens at serum dilutions of 1:50 (Table 1) and 1:200 (Table 2).

TABLE 1

Characteristics of the best predictive biomarkers at a dilution of 1:50.

| Antigen | Cox Regression | Pearson Correlation |
|---|---|---|
| 6'SLac | HR = 1.45 (p = 0.011) | r = −0.49 (p = 0.007) |
| SLeX | HR = 1.22 (p = 0.012) | r = −0.48 (p = 0.008) |
| GM3 | HR = 1.38 (p = 0.015) | r = −0.47 (p = 0.009) |
| BG-H1 | HR = 1.53 (p = 0.008) | r = −0.51 (p = 0.004) |
| GA2$_{di}$-37 | HR = 2.00 (p = 0.018) | r = −0.47 (p = 0.009) |
| LNnH-11 | HR = 1.70 (p = 0.004) | r = −0.41 (p = 0.028) |
| B$_{di}$ | HR = 0.68 (p = 0.044) | r = 0.30 (p = 0.118) |
| Ac—S-Tn(Thr)-G-G-07 | HR = 1.49 (p = 0.027) | r = −0.46 (p = 0.0118) |
| Ac—S-Tn(Thr)-G-G-24 | HR = 2.00 (p = 0.0213) | r = −0.52 (p = 0.0042) |
| BSM | HR = 1.36 (p = 0.0428) | r = −0.38 (p = 0.0411) |
| Lactose | HR = 1.88 (p = 0.0398) | r = −0.41 (p = 0.0257) |
| LNT-05 | HR = 1.19 (p = 0.0393) | r = −0.37 (p = 0.0474) |
| Fuc-b-04 | HR = 1.24 (p = 0.047) | r = −0.38 (p = 0.0414) |
| Fuc-b-22 | HR = 1.58 (p = 0.0247) | r = −0.49 (p = 0.0072) |
| Fuc-a-04 | HR = 1.37 (p = 0.067) | r = −0.45 (p = 0.0145) |
| Fuc-a-22 | HR = 1.39 (p = 0.098) | r = −0.42 (p = 0.027) |
| Galb1-6Man-a | HR = 1.29 (p = 0.0909) | r = −0.45 (p = 0.0139) |

TABLE 2

Characteristics of the best predictive biomarkers at a dilution of 1:200.

| Antigen | Cox Regression | Pearson Correlation |
|---|---|---|
| BG-H1 | HR = 1.39 (p = 0.0255) | r = −0.39 (p = 0.039) |
| B$_{di}$ | HR = 1.66 (p = 0.011) | r = 0.41 (p = 0.0259) |
| GA1-06 | HR = 0.73 (p = 0.0366) | r = 0.29 (p = 0.1297) |
| GA1-20 | HR = 0.68 (p = 0.0283) | r = 0.34 (p = 0.0723) |
| Gala1-4Galb | HR = 0.61 (p = 0.0164) | r = −0.37 (p = 0.051) |
| ManT | HR = 0.64 (p = 0.0206) | r = −0.29 (p = 0.1217) |
| pLNH-07 | HR = 4.2 (p = 0.0175) | r = −0.34 (p = 0.0742) |

FIGS. 1A-C include several examples of Kaplan-Meier survival curves that take into consideration the length of survival and whether or not the patient was still alive at the final time point. Patients were separated into two groups based on whether their antibody levels were above or below a cutoff, and the proportion of surviving patients was plotted over time. For example, patients with anti-sialyl LeX (anti-SLeX) levels about 9.6 had a 4 year survival of 8%, while patients with antibody levels below the cutoff had a 4 year survival of 60% (see FIG. 1A; p=0.0002). Kaplan-Meier curves were generated at a range of cutoffs for each array component to give an overall view of the performance of the biomarker.

For a small number of antigens, such as B$_{di}$, higher serum antibody levels correlated with improved survival (HR for B$_{di}$=0.68). For example, patients with anti-B$_{di}$ levels above a cutoff of 14.2 had a 4 year survival of 63%, while patients below the cutoff had a 4 year survival of 13% (see FIG. 1C). The difference in survival was statistically significant.

Combinations of antigens can provide even better predictive power. It is notable that many of the antigens identified have no correlation with the Halabi predicted survival and appear to be independent markers.

Efficacy Biomarkers

Changes in antibody levels were evaluated in 28 of the 29 patients. Sera were profiled before and after vaccination at dilutions of 1:50 and 1:200. A significant change was defined as greater than 2.6 fold based on previous studies. Significant antibody increases to a number of carbohydrate antigens were observed. All patients had at least one measurable change, and one patient had changes to 154 array components. The median number of changes per person was 14 at 1:50 and 8.5 at 1:200.

The most common changes were to the Forssman disaccharide (Forssman di-04; 18/28 patients at 1:200), GalNAcα1-3Galβ-(4/BSA) (A$_{di}$-04) (13/28 patients at 1:200), and GalNAcα1-3(Fucα1-2)Galβ1-(BG-A) (11/28 patients at 1:200). Changes ranged from 3 fold to 68 fold. Changes to tumor antigens also were observed, especially at the higher serum concentration (dilution of 1:50). Changes to the Tn antigen, the TF antigen, Sialylα2-3Galβ1-4 (Fucα1-3)GlcNAc-(SLex), SialylGalβ1-3(Fucα1-4)GlcNAcβ1-3Galβ1-4Glcβ-(SLeA), and Fucα1-2Galβ1-4 (Fucα1-3)GlcNAc-(LeY) were observed in 4-8 patients. Changes to other tumor antigens were detected, but less frequently (1-2 patients).

Several of the observed changes were to carbohydrate antigens known to be over-expressed on at least some patients' prostate tumors and their metastatic lesions, such as Tn, TF, SLeX, and LeY. Modest levels of expression of A$_{di}$ were observed on some prostate tumors.

Relationships between antibody responses and survival were also evaluated. Based on the Kaplan-Meier curve, patients with changes to Forssman di-04 at 1:200 showed a statistically significant correlation with improved survival (p=0.015; log rank). Antibody responses to Tn and TF also were associated with longer survival, while changes to A$_{di}$ did not show a significant correlation with improved survival in the subset of patients that were originally tested. There was no correlation between survival and the total number of changes for a given person.

EXAMPLE 2

This example demonstrates the identification of prognostic markers for prostate cancer.

There are a number treatment options for prostate cancer patients, but many of these treatments can cause significant side effects. In addition, many prostate tumors end up growing slowly and do not need treatment; however, it is very difficult to determine which patients should be treated aggressively and which are better served by a "watch and wait" approach. Better prognostic markers could be useful for aiding treatment decisions.

The Halabi nomogram provides a good estimation of life expectancy on treatment for patients with prostate cancer. It is most accurate for groups of patients, but also provides a reasonable projection on an individual basis. The nomogram combines many different measures of tumor aggressiveness and tumor burden, such as PSA levels and Gleason scores.

Antibody subpopulations in serum of patients were identified that correlate with the Halabi predicted survival. The best correlations are listed in Tables 3 and 4.

TABLE 3

Characteristics of the best prognostic biomarkers at a dilution of 1:50.

| Antigen | Pearson Correlation |
|---|---|
| GA2$_{di}$-37 | r = −0.39 (p = 0.036) |
| LNnH-11 | r = −0.38 (p = 0.0392) |
| SLeX | r = −0.45 (p = 0.0136) |
| Ac—S-Tn(Thr)-G-G-07 | r = −0.39 (p = 0.0353) |
| Ac—S-Tn(Thr)-G-G-24 | r = −0.42 (p = 0.022) |
| Fuc-a-04 | r = −0.48 (p = 0.0092) |
| Fuc-a-022 | r = −0.43 (p = 0.0187) |
| Fuc-b-04 | r = −0.37 (p = 0.0479) |
| Fuc-b-22 | r = −0.42 (p = 0.0233) |
| Galb1-6Man-a | r = −0.38 (p = 0.0412) |
| Man-a | r = −0.4529 (p = 0.014) |
| Isomaltose | r = −0.4413 (p = 0.017) |

TABLE 3-continued

Characteristics of the best prognostic biomarkers at a dilution of 1:50.

| Antigen | Pearson Correlation |
| --- | --- |
| Ara5 | r = −0.4119 (p = 0.026) |
| Man9 | r = −0.406 (p = 0.029) |
| GalNAc-b | r = −0.398 (p = 0.032) |
| BG-H2 | r = −0.396 (p = 0.033) |
| LacNAc (trimeric) | r = −0.3958 (p = 0.034) |
| Pk or Gb3 | r = −0.3913 (p = 0.036) |
| Cellobiose | r = −0.3881 (p = 0.037) |
| LNnT-14 | r = −0.3769 (p = 0.044) |
| Man$\alpha$1-6Man-a | r = −0.3742 (p = 0.046) |
| Gal3 | r = −0.372 (p = 0.047) |

TABLE 4

Characteristics of the best prognostic biomarkers at a dilution of 1:200.

| Antigen | Pearson Correlation |
| --- | --- |
| GA1-20 | r = 0.44 (p = 0.0158) |
| Gal$\alpha$1-4Galb | r = 0.39 (p = 0.0349) |
| ManT | r = 0.40 (p = 0.0304) |
| LSTb | r = 0.51793 (p = 0.004) |
| GalNAc-a-22 | r = 0.48366 (p = 0.008) |
| GalNAc-a-04 | r = 0.45712 (p = 0.013) |
| Forssman di-04 | r = 0.44945 (p = 0.014) |
| LNT-21 | r = 0.43332 (p = 0.019) |
| LeA-LeX | r = 0.43103 (p = 0.020) |
| Forssman di-31 | r = 0.37687 (p = 0.044) |
| Forssman di-21 | r = 0.36976 (p = 0.048) |

These biomarkers (i.e., antibody levels to the particular glycan or glycoprotein antigen) can be used as prognostic markers for prostate cancer. Since they are found in serum, they could be more readily used than the Halabi nomogram, which requires measurements of a variety of parameters including samples that are not easily accessed (biopsy samples).

EXAMPLE 3

This example describes experiments to validate the above-described findings with a larger set of patients.

A multicenter phase II trial was completed on the PROSTVAC-VF vaccine involving 112 patients. Patients received PROSTVAC-VF therapy or control vectors. The inclusion criteria, vaccine construct, and therapeutic protocol for this trial were essentially the same as the 29 patients described in Example 1.

Anti-glycan antibody populations in sera before and 3 months after vaccination at both 1:50 and 1:200 were be profiled using the array technology described in Example 1. Combined antibody levels (anti-Ig), as well as IgG and IgM separately, were examined. All clinical data was blinded until after the profiling was complete. Once the survival data was unblinded, the relationships between antibody signals and survival were analyzed. Pearson correlations, hazard ratios, Kaplan-Meier curves, ROC curves, and each of their corresponding p-values were evaluated as discussed in Example 1. In addition, the relationships between changes and survival were evaluated. Analysis of the relationships between biomarker levels and survival in the control arm allowed the determination whether the markers are general prognostic markers or specific markers for vaccine therapy.

Tables 5 and 6 indicate the hazard ratios, Pearson correlations with overall survival, and associated p-values for the best predictive (Table 5) and efficacy (Table 6) biomarkers associated with this study.

TABLE 5

Characteristics of the best predictive biomarkers.

| Array component | Best dilution | Measurement | Pearson correlation | | Cox regression | |
| --- | --- | --- | --- | --- | --- | --- |
| | | | r | p-value | Hazard Ratio | p-value |
| LNnH - 11 | 1:200 | Pre-vaccination | −0.2611 | 0.023 | 2.5276 | 0.003 |
| 6'Slac | 1:50 | Pre-vaccination | −0.2398 | 0.037 | 1.55682 | 0.0051 |
| GM3 | 1:50 | Pre-vaccination | −0.2315 | 0.044 | 1.46536 | 0.0067 |
| Rha-a | 1:50 | Pre-vaccination | 0.1881 | 0.104 | 0.7291 | 0.029 |
| Ac-S-Tn(Ser)-S-G - 33 | 1:50 | Pre-vaccination | 0.2719 | 0.018 | 0.6705 | 0.0044 |
| Blood Group A (IgM) | 1:50 | Pre-vaccination | 0.37 | 0.0009 | 0.79 | 0.0009 |
| Ac-S-Tn(Ser)-S-G - 22 | 1:200 | Pre-vaccination | 0.20899 | 0.070 | 0.7808 | 0.032 |

TABLE 6

Characteristics of the best efficacy biomarkers.

| Array component | Best dilution | Measurement | Pearson correlation | | Cox regression | |
| --- | --- | --- | --- | --- | --- | --- |
| | | | r | p-value | Hazard Ratio | p-value |
| Forssman-04 | 1:200 | Change | 0.2477 | 0.031 | 0.8083 | 0.048 |
| fetuin | 1:50 | Change | 0.2656 | 0.020 | 0.7841 | 0.043 |
| A-LeB - hexa | 1:50 | Change | 0.2940 | 0.010 | 0.7952 | 0.035 |

Serum IgM antibody levels to the blood group A trisaccharide (BG-A) consistently demonstrated positive correlations with overall survival in a variety of statistical models (see FIG. 1D). Median survival was more than a year longer in subjects with abundant pre-existing IgM antibodies for BG-A. The highest quartile of subjects with anti-BG-A IgM antibodies prior to vaccination survived nearly twice as long as the lowest quartile. Post-vaccination survival correlated strongly with pre-vaccination BG-A IgM (HR=0.79, p=0.00085). ROC analysis showed an AUC of 0.77 for post-vaccination survival of at least 30 months. BG-A IgM antibodies appear to be an independent prognostic marker without correlation to Halabi predicted survival, Gleason score, age, or PSA level.

As was observed with the initial study described in Example 1, patients frequently showed humoral responses to the Forssman disaccharide. Changes in binding to Forssman disaccharide were measured best at a serum dilution of 1:200. Robust changes to Forssman disaccharide correlated with longer post-vaccination survival. The median survival of patients with at least a four-fold increase in anti-Forssman disaccharide antibodies was 8 months longer than the median survival of patients with little or no response to Forssman disaccharide (p=0.005). Moreover, among the patients with responses to Forssman disaccharide, odds-ratio calculations demonstrated that larger responses to Forssman disaccharide were associated with greater likelihood of long-term survival (≥3.5 years post-vaccination). Patients with the highest likelihood of surviving at least 3.5 years had six to ten-fold increases in antibodies to Forssman disaccharide, which were associated with eight-fold better probability of living at least 3.5 years post-vaccination than patients with lower responses.

Antibody responses to the Forssman antigen (e.g., Forssman disaccharide) were independent risk factors that did not correlate with overall titers to viral vectors, T-cell responses, Halabi predicted survival, age, PSA level, or Gleason score.

Since patients with antibody responses to the Forssman antigen (e.g., Forssman disaccharide) and BG-A have longer survival, the efficacy of the vaccine may be improved by purposely enhancing responses to Forssman and/or BG-A and/or stimulating responses to Forssman and/or BG-A in all patients.

Interestingly, control patients also showed increases in antibodies for BG-A after inoculation with inactive, wild-type viral vectors. Similarly, control patients showed increases in antibodies for the Forssman disaccharide after inoculation with inactive, wild-type viral vectors. Survival in control patients, however, was not correlated with responses to Forssman disaccharide. This indicates that increases in Forssman disaccharide alone are not general prognostic indicators. Instead, it shows that these responses are specific markers of efficacy for the vaccine.

While not wishing to be bound by any particular theory, the Forssman antigen, a fragment or substructure of the Forssman antigen, a larger glycan and/or glycoprotein antigen that includes the fragment or substructure, or an antigen with a similar structure (e.g., core 5) and/or BG-A or a derivative thereof may be located on some poxvirus vector vaccines (e.g., PROSTVAC-VF and ALVAC-HIV).

To test this theory, the expression of BG-A and the Forssman antigen on vaccinia and fowlpox viruses was evaluated using ELISA and a competition assay. The expression of BG-A and the Forssman antigen was confirmed on both viral vectors. The BG-A and Forssman antigen carbohydrates likely are acquired by carry-over from their host cells (chicken embryo dermal cells) in a manner similar to that reported for influenza viruses propagated in chicken cells. Consistent with this, chickens are known to synthesize both Forssman antigen and BG-A. Based on these results, it appears that the responses to BG-A and the Forssman antigen induced by PROSTVAC-VF are a result of the viral vector rather than a response to PSA or a response derived from antigen-spreading.

Implications of these results also extends to other vaccines. Several poxvirus-based cancer vaccines are in clinical trials, such as PANVAC and rV-NY-ESO-1. Oncolytic poxviruses also are being developed (see, e.g., Ziauddin et al., *Gene Ther.*, 17: 550-559 (2010); and Kirn et al., *Nature Reviews Cancer*, 9: 64-71 (2009)), and povirus-based vaccines are being investigated to prevent infection of many pathogens (e.g., ALVAC-HIV). Many of these vectors are produced in chicken embryo dermal cells, and antibodies to BG-A and the Forssman antigen likely are relevant to their clinical efficacy.

Since the results indicate that glycan composition and consistency are a critical feature of vaccine potency, the choice of host cell may significantly impact clinical outcomes for pox-virus based vaccines. Additionally, glycan analysis of viral vectors could serve as a quality control assessment for virus-based vaccines.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for predicting the clinical response to a viral vector-based vaccine in a patient and treating prostate cancer in the patient, the method comprising:
   obtaining a serum sample from a patient having prostate cancer who has not been previously administered the viral vector-based vaccine, wherein the viral vector-based vaccine comprises a primer vaccination of a recombinant vaccinia virus encoding prostate specific antigen (PSA), B7.1, LFA-3, and ICAM-1;
   assaying the serum sample to determine the levels of antibodies in the patient to at least one glycan and/or glycoprotein antigen selected from the group consisting of Forssman antigen and GalNAcα1-3(Fucα1-2)Galβ- (BG-A);
   comparing the determined levels of antibodies to the at least one glycan and/or glycoprotein antigen to a control and predicting the clinical response to the viral vector-based vaccine in the patient; and
   treating the prostate cancer by administering the viral vector-based vaccine to the patient.

2. The method of claim 1, wherein the antibodies are selected from the group consisting of IgG, IgM, IgA, IgD, IgE, and combinations thereof.

3. The method of claim 1, wherein the serum sample is assayed to determine the levels of IgM antibodies to BG-A.

4. A method for determining the immune response to a viral vector-based vaccine in a patient and treating prostate cancer in the patient, the method comprising:
   obtaining a first serum sample from a patient having prostate cancer who has not been previously administered the viral vector-based vaccine, wherein the viral vector-based vaccine comprises a primer vaccination of a recombinant vaccinia virus encoding prostate specific antigen (PSA), B7.1, LFA-3, and ICAM-1;

obtaining a second serum sample from the patient after administration of the viral vector-based vaccine, assaying the first and second serum samples to determine the first and second levels of antibodies, respectively, to at least one glycan and/or glycoprotein antigen selected from the group consisting of Forssman antigen and GalNAcα1-3(Fucα1-2)Galβ-(BG-A);

comparing the determined first and second levels of antibodies to the at least one glycan and/or glycoprotein antigen and determining the immune response to the viral vector-based vaccine in the patient; and treating the prostate cancer in the patient by administering a booster vaccine comprising a recombinant fowlpox virus encoding PSA, B7.1, LFA-3, and ICAM-1 to the patient.

5. The method of claim 4, wherein the first and second serum samples are assayed to determine the levels of antibodies to the Forssman antigen.

6. The method of claim 4, wherein the first and second serum samples are assayed to determine the levels of antibodies to BG-A.

7. The method of claim 4, wherein the antibodies are selected from the group consisting of IgG, IgM, IgA, IgD, IgE, and combinations thereof.

8. The method of claim 4, wherein the first serum sample is assayed to determine the levels of IgG, IgM, and IgA antibodies to the Forssman antigen.

9. A method for predicting the clinical response to a viral vector-based vaccine in a patient and treating prostate cancer in the patient, the method comprising:

administering the viral vector-based vaccine to the patient, wherein the viral vector-based vaccine comprises a primer vaccination of a recombinant vaccinia virus encoding prostate specific antigen (PSA), B7.1, LFA-3, and ICAM-1;

obtaining a serum sample from the patient to which the vaccine was administered;

assaying the serum sample to determine the levels of antibodies in the patient to at least one glycan and/or glycoprotein antigen selected from the group consisting of Forssman antigen and GalNAcα1-3 (Fucα1-2)Galβ-(BG-A);

comparing the determined levels of antibodies to the at least one glycan and/or glycoprotein antigen to a control and predicting the clinical response to the viral vector-based vaccine in the patient; and treating the prostate cancer in the patient by administering a booster vaccine comprising a recombinant fowlpox virus encoding PSA, B7.1, LFA-3, and ICAM-1 to the patient.

10. The method of claim 9, wherein the serum sample is assayed to determine the levels of antibodies to the Forssman antigen.

11. The method of claim 9, wherein the serum sample is assayed to determine the levels of antibodies to BG-A.

12. The method of claim 9, wherein the serum sample is from a patient at least 2 months after the administration of the viral vector-based vaccine.

13. The method of claim 4, wherein assaying the first and second serum samples to determine the first and second levels of antibodies, respectively, to the at least one glycan and/or glycoprotein antigen comprises presenting the at least one glycan and/or glycoprotein antigen on an antigen surface, contacting the antigen surface with the first and second serum samples, and measuring the levels of antibodies to the at least one glycan and/or glycoprotein antigen in the first and second serum samples.

14. The method of claim 13, wherein the Forssman antigen is presented on an antigen surface at low density.

15. The method of claim 9, wherein assaying the serum sample to determine the levels of antibodies in the patient to the at least one glycan and/or glycoprotein antigen comprises presenting the at least one glycan and/or glycoprotein antigen on an antigen surface, contacting the antigen surface with the serum sample, and measuring the levels of antibodies to the at least one glycan and/or glycoprotein antigen in the serum sample.

16. The method of claim 15, wherein the Forssman antigen is presented on an antigen surface at low density.

17. The method of claim 1, further comprising administering one or more booster vaccinations of a recombinant fowlpox virus encoding PSA, B7.1, LFA-3, and ICAM-1 to the patient.

18. The method of claim 1, wherein levels of antibodies in the patient to BG-A is determined.

19. The method of claim 4, wherein the recombinant fowlpox virus encoding PSA, B7.1, LFA-3, and ICAM-1 is administered at least two times.

20. The method of claim 4, wherein the second serum sample is from a patient at least 2 months after the administration of the viral vector-based vaccine.

21. The method of claim 9, wherein the recombinant fowlpox virus encoding PSA, B7.1, LFA-3, and ICAM-1 is administered at least two times.

22. The method of claim 9, wherein the antibodies are selected from the group consisting of IgG, IgM, IgA, IgD, IgE, and combinations thereof.

23. The method of claim 9, wherein the serum sample is assayed to determine the levels of IgG, IgM, and IgA antibodies to the Forssman antigen.

24. The method of claim 9, comprising obtaining the serum sample from the patient to which one or more booster vaccines comprising recombinant fowlpox virus encoding PSA, B7.1, LFA-3, and ICAM-1 had been administered.

25. A method for predicting the clinical response to a viral vector-based vaccine in a patient and treating prostate cancer in the patient, the method comprising:

obtaining a first serum sample from a patient having prostate cancer, assaying the first serum sample to determine the first levels of antibodies in the patient to GalNAcα1-3 (Fucα1-2)Galβ-(BG-A) and Forssman antigen;

administering a primer vaccination of a recombinant vaccinia virus encoding prostate specific antigen (PSA), B7.1, LFA-3, and ICAM-1 to the patient;

obtaining a second serum sample from the patient after the primer vaccination was administered;

assaying the second serum sample to determine the second levels of antibodies in the patient to the Forssman antigen;

comparing the first and second levels of antibodies to the Forssman antigen and predicting the clinical response to the viral vector-based vaccine in the patient; and treating the prostate cancer in the patient by administering one or more booster vaccines comprising recombinant fowlpox virus encoding PSA, B7.1, LFA-3, and ICAM-1 to the patient.

26. The method of claim 4, wherein the second serum sample is assayed to determine the levels of IgG, IgM, and IgA antibodies to the Forssman antigen.

* * * * *

SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ala
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 1

Xaa Xaa Ser Gly
1

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Gly
<220> FEATURE:
<221> NAME/KEY: CARBOHYD
<222> LOCATION: (3)..(3)
<223> OTHER INFORMATION: Xaa is Thr linked to GalNAcAlpha

<400> SEQUENCE: 2

Xaa Val Xaa Ser Ala Gly
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Pro
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 3

Xaa Xaa Thr Gly
1

<210> SEQ ID NO 4
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser

<400> SEQUENCE: 4

```
Xaa Ser Ser Gly
1

<210> SEQ ID NO 5
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Ser linked to GalBeta1-3GalNAcAlpha

<400> SEQUENCE: 5

Xaa Xaa Ser Gly
1

<210> SEQ ID NO 6
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser

<400> SEQUENCE: 6

Xaa Thr Ser Gly
1

<210> SEQ ID NO 7
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Ser linked to GalNAc alpha
<220> FEATURE:
<221> NAME/KEY: CARBOHYD
<222> LOCATION: (2)..(2)
<223> OTHER INFORMATION: Xaa is Ser linked to GalNAcAlpha

<400> SEQUENCE: 7

Xaa Xaa Ser Gly
1

<210> SEQ ID NO 8
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
```

```
<222> LOCATION: (2)..(2)
<223> OTHER INFORMATION: Xaa is Thr linked to GalNAcAlpha

<400> SEQUENCE: 8

Xaa Xaa Ala Gly
1

<210> SEQ ID NO 9
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 9

Xaa Xaa Gly Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 10

Xaa Xaa Ser Gly
1

<210> SEQ ID NO 11
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Thr linked to GalNAcAlpha
<220> FEATURE:
<221> NAME/KEY: CARBOHYD
<222> LOCATION: (3)..(3)
<223> OTHER INFORMATION: Xaa is Thr linked to GalNAcAlpha

<400> SEQUENCE: 11

Xaa Xaa Xaa Gly
1

<210> SEQ ID NO 12
<211> LENGTH: 4
<212> TYPE: PRT
```

```
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (2)..(2)
<223> OTHER INFORMATION: Xaa is Thr linked to GalNAcAlpha
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 12

Xaa Xaa Val Gly
1

<210> SEQ ID NO 13
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Ser
<220> FEATURE:
<221> NAME/KEY: CARBOHYD
<222> LOCATION: (1)..(1)
<223> OTHER INFORMATION: Xaa is Ser linked to GalNAcAlpha
<220> FEATURE:
<221> NAME/KEY: CARBOHYD
<222> LOCATION: (2)..(2)
<223> OTHER INFORMATION: Xaa is Ser linked to GalNAcAlpha
<220> FEATURE:
<221> NAME/KEY: CARBOHYD
<222> LOCATION: (3)..(3)
<223> OTHER INFORMATION: Xaa is Ser linked to GalNAcAlpha

<400> SEQUENCE: 13

Xaa Xaa Xaa Gly
1

<210> SEQ ID NO 14
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Thr
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 14

Xaa Xaa Pro Gly
1

<210> SEQ ID NO 15
<211> LENGTH: 4
<212> TYPE: PRT
<213> ORGANISM: Artificial Sequence
<220> FEATURE:
<223> OTHER INFORMATION: Synthetic
<220> FEATURE:
```

```
<221> NAME/KEY: ACETYLATION
<222> LOCATION: (1)..(1)
<223> OTHER INFORMATION: Xaa is Ac-Thr
<220> FEATURE:
<221> NAME/KEY: CARBOHYD
<222> LOCATION: (1)..(1)
<223> OTHER INFORMATION: Xaa is Thr linked to GalNAcAlpha
<220> FEATURE:
<221> NAME/KEY: CARBOHYD
<222> LOCATION: (2)..(2)
<223> OTHER INFORMATION: Xaa is Thr linked to GalNAcAlpha
<220> FEATURE:
<221> NAME/KEY: CARBOHYD
<222> LOCATION: (3)..(3)
<223> OTHER INFORMATION: Xaa is Thr linked to GalNAcAlpha

<400> SEQUENCE: 15

Xaa Xaa Xaa Gly
1

<210> SEQ ID NO 16
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: ACETYLATION
<222> LOCATION: (1)..(1)
<223> OTHER INFORMATION: Xaa is Ac-Val
<220> FEATURE:
<221> NAME/KEY: CARBOHYD
<222> LOCATION: (2)..(2)
<223> OTHER INFORMATION: Xaa is Thr linked to GalNAcAlpha

<400> SEQUENCE: 16

Xaa Xaa Ser Gly
1

<210> SEQ ID NO 17
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: CARBOHYD
<222> LOCATION: (11)..(11)
<223> OTHER INFORMATION: Xaa is Thr linked to GalBeta1-3GalNAcAlpha

<400> SEQUENCE: 17

Asp Thr Val Pro Leu Pro Thr Ala His Gly Xaa Ser Ala Ser Ser Thr
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: CARBOHYD
<222> LOCATION: (11)..(11)
<223> OTHER INFORMATION: Xaa is Thr linked to GalBeta1-3GalNAcAlpha
<220> FEATURE:
<221> NAME/KEY: CARBOHYD
<222> LOCATION: (12)..(12)
<223> OTHER INFORMATION: Xaa is Ser linked to GalBeta1-3GalNAcAlpha

<400> SEQUENCE: 18
```

-continued

```
Asp Thr Val Pro Leu Pro Thr Ala His Gly Xaa Xaa Ala Ser Ser Thr
1               5                   10                  15
Gly

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Asp Thr Val Pro Leu Pro Thr Ala His Gly Thr Ser Ala Ser Ser Thr
1               5                   10                  15
Gly

<210> SEQ ID NO 20
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: CARBOHYD
<222> LOCATION: (12)..(12)
<223> OTHER INFORMATION: Xaa is Ser linked to GalBeta1-3GalNAcAlpha

<400> SEQUENCE: 20

Asp Thr Val Pro Leu Pro Thr Ala His Gly Thr Xaa Ala Ser Ser Thr
1               5                   10                  15
Gly

<210> SEQ ID NO 21
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: CARBOHYD
<222> LOCATION: (7)..(7)
<223> OTHER INFORMATION: Xaa is Thr linked to GalBeta1-3GalNAcAlpha

<400> SEQUENCE: 21

Asp Thr Val Pro Leu Pro Xaa Ala His Gly Thr Ser Ala Ser Ser Thr
1               5                   10                  15
Gly
```